US009562247B2

(12) United States Patent
Takaha et al.

(10) Patent No.: US 9,562,247 B2
(45) Date of Patent: Feb. 7, 2017

(54) METHOD FOR INDUSTRIALLY PRODUCING CYCLIC-STRUCTURE-CONTAINING BRANCHED GLUCAN

(75) Inventors: Takeshi Takaha, Osaka (JP); Kouji Odan, Osaka (JP); Michiyo Yanase, Osaka (JP); Iwao Kojima, Osaka (JP); Tsunehisa Akiyama, Osaka (JP)

(73) Assignee: Ezaki Glico Co., Ltd., Osaka-shi, Osaka (JP)

( * ) Notice: Subject to any disclaimer, the term of this patent is extended or adjusted under 35 U.S.C. 154(b) by 781 days.

(21) Appl. No.: 13/992,205

(22) PCT Filed: Dec. 2, 2011

(86) PCT No.: PCT/JP2011/006778
§ 371 (c)(1),
(2), (4) Date: Aug. 19, 2013

(87) PCT Pub. No.: WO2012/077322
PCT Pub. Date: Jun. 14, 2012

(65) Prior Publication Data
US 2013/0323799 A1    Dec. 5, 2013

(30) Foreign Application Priority Data
Dec. 7, 2010    (JP) ................... 2010-272869

(51) Int. Cl.
C12P 19/04    (2006.01)
C12P 19/18    (2006.01)
(Continued)

(52) U.S. Cl.
CPC ............. *C12P 19/04* (2013.01); *C12P 19/18* (2013.01); *C12Y 204/01018* (2013.01)

(58) Field of Classification Search
None
See application file for complete search history.

(56) References Cited

U.S. PATENT DOCUMENTS 6,248,566 B1 *   6/2001   Imanaka ............. C08B 37/0009
                                                         435/72
7,041,484 B1 *   5/2006   Baga ...................... C12N 9/107
                                                        435/193
(Continued)

FOREIGN PATENT DOCUMENTS

EP    0 710 674 A2    5/1996
JP    08-134104 A    5/1996
(Continued)

OTHER PUBLICATIONS

Japanease Patent Gazette No. 3107358.*
Unno JP10-117671, May 12, 1998.*

*Primary Examiner* — Blaine Lankford
*Assistant Examiner* — Lauren K Van Buren
(74) *Attorney, Agent, or Firm* — Seed IP Law Group LLP

(57) ABSTRACT

An object of the present invention is to provide a method for industrially producing a branched glucan having a cyclic structure. The method for producing a branched glucan having a cyclic structure comprises the steps of: (1) preparing a mixed liquid which contains a branching enzyme in which starch granules are suspended at a concentration of 5% by weight or more and 50% by weight or less, and allowing the branching enzyme to act on starch in the starch granules, wherein a temperature of the mixed liquid at the time of preparation is 0° C. or higher and not higher than the gelatinization starting temperature of the starch granule; and (2) elevating the temperature of the mixed liquid to 85° C. or higher and 129° C. or lower, wherein in the method, none
(Continued)

of α-amylase, β-amylase, amyloglucosidase and αtransglucosidase is added to the mixed liquid.

11 Claims, 2 Drawing Sheets

(51) Int. Cl.
*A23L 1/30* (2006.01)
*A23L 1/307* (2006.01)

(56) References Cited

U.S. PATENT DOCUMENTS

2004/0014961 A1    1/2004  Backer et al.
2006/0134006 A1*   6/2006  Tester .................... A61K 47/36
                                                    424/45
2010/0047891 A1*   2/2010  Yanase ................. C12N 9/1051
                                                    435/193

FOREIGN PATENT DOCUMENTS

JP      10-117671 A     5/1998
JP       3107358 B2     9/2000
JP      2004-161998 A   6/2004

\* cited by examiner

METHOD FOR INDUSTRIALLY PRODUCING CYCLIC-STRUCTURE-CONTAINING BRANCHED GLUCAN

TECHNICAL FIELD

The present invention relates to a production method for obtaining a cyclic-structure-containing branched glucan at an industrially high yield. In other words, the present invention relates to a production method for obtaining a cyclic-structure-containing branched glucan at an industrially high yield, in which generation of a non-cyclic glucan byproduct (i.e., a byproduct having a reducing end) is small.

BACKGROUND ART

A cyclic-structure-containing branched glucan produced by allowing a branching enzyme to act on a starch has following excellent properties: it has no reducing end; their solubility in water is higher as compared with those of natural unmodified starch; viscosity of its solution is low; and retrogradation which is observed for natural unmodified starch is difficult to occur. The cyclic-structure-containing branched glucan has been developed and utilized as a useful substitute substance for starch.

The cyclic-structure-containing branched glucan can be produced by heating starch such as waxy corn starch to a temperature that is the gelatinization starting temperature or higher of the starch to dissolve the starch, then, cooling the starch solution to a temperature at which a branching enzyme can react therewith and, thereafter, adding a branching enzyme to this starch solution to allow to act thereon (Patent Document 1). However, in this method, the starch solution becomes a rice cake state during cooling, and flowability cannot be ensured. For example, Example 1 in paragraph 0119 of Patent Document 1 describes an experiment in a small scale at a laboratory level, in which a small amount of waxy corn starch (5 g) is suspended in 40 ml of a buffer solution to gelatinize the starch at 100° C. and, after allowing it to cool to 50° C., a branching enzyme is allowed to act thereon. Although the description of a detailed procedure is not given in paragraph 0119 of Patent Document 1, a working step which is not industrially practical, such as inserting a spoon into a reaction tube to forcibly stir a starch solution having no flowability (i.e., gel), is necessary for mixing an enzyme and a substrate in such an experiment at a laboratory level, and actually, the inventors of the subject matters described in Patent Document 1 have performed the work of forcible stirring when they performed the experiment in paragraph 0119 thereof. It is also clear from FIG. 2 of TAKATA et al., Journal of fermentation and bioengineering Vol. 84, No. 2, 119-123, 1997 that such a high concentration starch solution has no flowability. For this reason, if it is attempting to industrially produce a cyclic-structure-containing branched glucan by this method, since a starch solution has no flowability, clogging of a pipe for transporting the starch solution to a reaction vessel is caused so that the starch solution for performing an enzymatic reaction cannot be transported to the reaction vessel.

For this reason, when a cyclic-structure-containing branched glucan is industrially produced, the following method is adopted (Patent Document 2): feeble α-amylase is added to a suspension of starch, the suspension is heated to a temperature that is the gelatinization starting temperature of the starch or higher, to proceed dissolution of the starch and low molecularization of the starch due to partial hydrolysis of the starch simultaneously, and thus, a starch-gelatinized liquid having ensured flowability is prepared and, thereafter, a branching enzyme (also described as BE in the present specification) is added to this starch-gelatinized liquid to allow to act thereon. However, in such a method of using both of thermal gelatinization and hydrolysis, hydrolysis of the starch occurs and, as a result, a non-cyclic glucan having a reducing end is generated. For this reason, in this method, only a mixture of a cyclic-structure-containing branched glucan having no reducing end and a non-cyclic glucan having a reducing end could be obtained. The cyclic-structure-containing branched glucan having no reducing end will not be colored even when heated with an amino acid or a protein, but the non-cyclic glucan having a reducing end has a defect that it will be colored when heated with an amino acid or a protein. Furthermore, it is extremely difficult to industrially isolate the cyclic-structure-containing branched glucan having no reducing end, from this mixture.

A method for producing a cyclic-structure-containing branched glucan having no defect as described above and no reducing end, at an industrial scale, with high purity has not been known so far. That is, a method for producing a cyclic-structure-containing branched glucan, wherein a glucan having a reducing end is not generated as a byproduct, that is, a method for industrially producing a cyclic-structure-containing branched glucan without using α-amylase, has not been known.

In addition, Patent Document 3 describes a method for producing a highly branched glucan using raw starch. However, the purpose of Patent Document 3 is producing a highly branched glucan, and the highly branched glucan has a reducing end, and the purpose of Patent Document 3 is not producing a glucan having no reducing end. Further, a reducing sugar is included in the product described in Patent Document 3.

PRIOR ART DOCUMENTS

Patent Documents

Patent Document 1: Japanese Patent Gazette No. 3107358
Patent Document 2: Japanese Laid-Open Publication No. 10-117671
Patent Document 3: Japanese Laid-Open Publication No. 2004-161998

SUMMARY OF THE INVENTION

Problems to Be Solved by the Invention

The present invention intends to solve the aforementioned problems, and an objective thereof is to provide a method for producing a cyclic-structure-containing branched glucan, wherein a non-cyclic glucan (i.e., a byproduct having a reducing end) is not generated as a byproduct.

Means for Solving the Problems

As a result of diligent study to solve the aforementioned problems, the present inventors found that, not by heating and gelatinizing starch in advance, but by adding a BE to a starch suspension at a gelatinization starting temperature or lower and, thereafter, elevating the temperature of the starch suspension to a gelatinization starting temperature or higher, a cyclic-structure-containing branched glucan can be produced in the case where flowability of a reaction mixed liquid is ensured without combined use of a hydrolysis reaction using α-amylase. Based on these findings, the present inventors completed the present invention. Further, the present inventors have found that when the reaction temperature exceeds at least 80° C. in the reaction step without combined use of α-amylase, the yield of a cyclic glucan is greatly improved, and thus completed the present invention.

The present invention relates to a method for producing a cyclic-structure-containing branched glucan. The cyclic-structure-containing branched glucan refers to a glucan in which a part of a branched glucan structure forms a ring. The "cyclic-structure-containing branched glucan" and the "branched glucan having a cyclic structure" are used exchangeably. Herein, "a part of a branched glucan structure forms a ring" means a structure in which a saccharide chain in the glucan has a cyclic-structure, and at least one branched structure based on an α-1,6 bond and an α-1,4 bond, and at least one α-1,6 bond is present in the saccharide chain constituting the cyclic-structure thereof. A schematic view of generation of a cyclic-structure-containing glucan by BE is shown in FIG. 2. 1 in FIG. 2 shows a simplified structure of amylopectin in starch, that is a substrate. Amylopectin has a structure such that parts having many branches are connected with relatively long linear parts. A BE acts on this linear part to cut an α-1,4-bond, and binds a reducing end to another place on amylopectin with an α-1,6-bond. As a result, cyclic-structure-containing branched glucans having a variety of structures are formed. Examples of the structure of the resulting cyclic-structure-containing branched glucan are shown in 2 to 4 in FIG. 2. Due to the mechanism of action of BE, the cyclic-structure-containing branched glucan of the present invention has no reducing end.

It can be said that the cyclic-structure-containing branched glucan of the present invention has a structure in which a part corresponding to a reducing end part of a normal branched glucan is bound on the branched glucan with an α-1,6 bond. It can be also said that the cyclic-structure-containing branched glucan of the present invention is such that a branched structure is bound to a cyclic-structure having at least one α-1,6 bond.

In the preferred embodiments of the present invention, for example, the followings are provided:

Item 1

A method for producing a branched glucan having a cyclic structure comprising the steps of:

(1) preparing a mixed liquid which comprises a branching enzyme in which starch granules are suspended at a concentration of 5% by weight or more and 50% by weight or less, and allowing the branching enzyme to act on starch in the starch granules, wherein a temperature of the mixed liquid at the time of preparation is 0° C. or higher and not higher than the gelatinization starting temperature of the starch granules; and (2) elevating the temperature of the mixed liquid to 85° C. or higher and 129° C. or lower, wherein in the method, none of α-amylase, β-amylase, amyloglucosidase and α transglucosidase is added to the mixed liquid.

Item 2

The method according to Item 1, wherein the temperature of the mixed liquid at the time of preparation in the step (1) is 0 to 67.5° C., and the method further includes, thereafter and before the step (2), a step of raising the temperature of the mixed liquid to a temperature which is higher than the temperature of the mixed liquid at the time of preparation and is within a range of 30 to 75° C. to thereby allow the branching enzyme to act on starch in the starch granules.

Item 3

The method according to Item 1, wherein the temperature of the mixed liquid at the time of preparation in the step (1) is 15 to 67.5° C., and the method further includes, thereafter and before the step (2), a step of raising the temperature of the mixed liquid to a temperature which is higher than the temperature of the mixed liquid at the time of preparation and is within a range of 30 to 75° C. to thereby allow the branching enzyme to act on starch in the starch granules.

Item 4

The method according to Item 1, wherein the temperature of the mixed liquid at the time of preparation in the step (1) is 20 to 50° C., and the method further includes a step of, thereafter and before the step (2), raising the temperature of the mixed liquid to a temperature which is higher than the temperature of the mixed liquid at the time of preparation and is within a range of 40 to 75° C. to thereby allow the branching enzyme to act on starch in the starch granules.

Item 5

The method according to Item 1, wherein the temperature of the mixed liquid at the time of preparation in the step (1) is 20 to 40° C., and the method further includes, thereafter and before the step (2), a step of raising the temperature of the mixed liquid to a temperature which is higher than the temperature of the mixed liquid at the time of preparation and is within a range of 50 to 75° C. to thereby allow the branching enzyme to act on starch in the starch granules.

Item 6

The method according to Item 1, wherein after the mixed liquid is prepared in the step (1) the temperature raising in the step (2) is completed within a period of time of 10 seconds or longer and 72 hours or shorter, and the method further includes, after the step (2), a step of lowering the temperature of the mixed liquid to 0° C. to 100° C. and, then, adding a branching enzyme to allow to act at 0° C. to 100° C.

Item 7

The method according to Item 1, wherein after the mixed liquid is prepared in the step (1) the temperature raising in the step (2) is completed within a period of time of 1 second or longer and 20 seconds or shorter, and the method further includes, after the step (2), a step of lowering the temperature of the mixed liquid to 0° C. to 100° C. and, then, adding a branching enzyme to allow to act at 0° C. to 100° C.

Item 8

The method according to Item 1, wherein after the mixed liquid is prepared in the step (1) the temperature raising in the step (2) is completed within a period of time of 1 second or longer and 20 seconds or shorter, and the method further includes, after the step (2), a step of lowering the temperature of the mixed liquid to 0° C. to 100° C. and, then, adding a branching enzyme to allow to act at 50° C. to 100° C.

Item 9

The method according to any one of Items 1 to 8, further comprising a step of removing insolubles from the mixed liquid, after the step (2).

Item 10

The method according to any one of Items 1 to 9, wherein in the step (2), the branching enzyme has an activity.

Item 11

The method according to any one of Items 1 to 10, wherein the branching enzyme is an *Aquifex aeolicus*-derived branching enzyme or a *Rhodothermus obamensis*-derived branching enzyme.

Effects of the Invention

In a reaction mixed liquid containing a conventional cyclic-structure-containing branched glucan (also referred to as cyclic cluster dextrin (CCD)) produced by the method of Patent Document 1 (Japanese Patent Gazette No. 3107358), a linear glucan generated by an α-amylase reaction and a non-cyclic branched glucan (which is unable to undergo cyclization action of BE because a glucan becomes a cluster unit due to action of α-amylase) are mixed therein in addition to a pure cyclic-structure-containing branched glucan.

To the contrary, in the present application which does not use α-amylase, only a pure cyclic-structure-containing branched glucan is generated. Accordingly, the reducing power of the cyclic-structure-containing branched glucan-containing liquid generated is completely zero. Further, the resulting cyclic-structure-containing branched glucan will not be retrograded. Further, as in Examples, there is a tendency that a weight-average molecular weight is smaller than that of the conventional CCD. This tendency is also derived from without using α-amylase in the method of the present invention.

In an embodiment of a two-step reaction method of the present invention, a cyclic-structure-containing branched glucan can be produced at a relatively small amount of enzyme according to the method of the present invention.

Since the method of the present invention can utilize an instantaneous continuous reaction method, which previously could be utilized only in production of dextrin, the method has an advantage that new equipment investment is unnecessary.

MODE FOR CARRYING THE INVENTION

Figure 1:
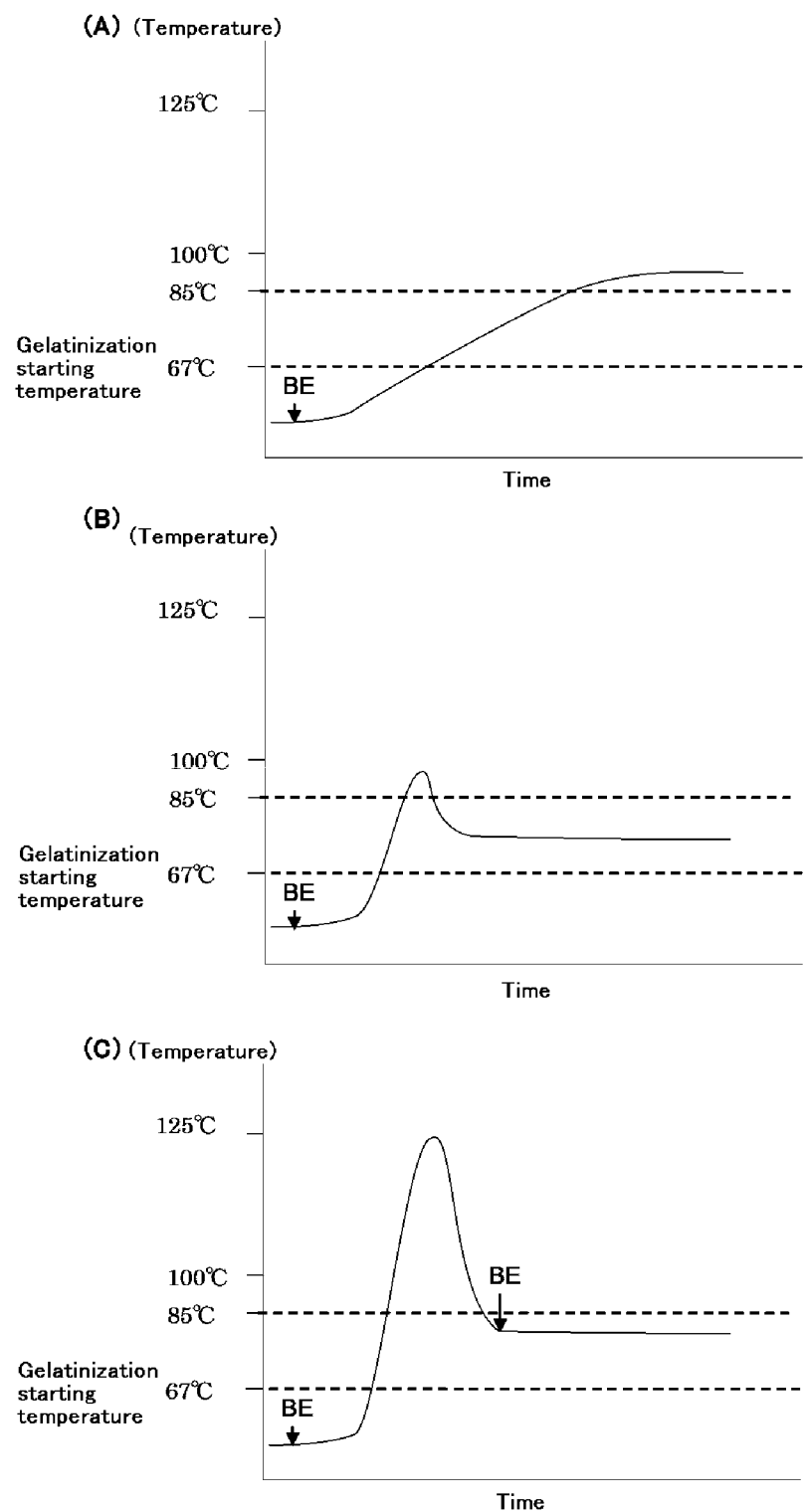
FIG. 1 is a diagram showing examples of a change in temperature of a reaction mixed liquid and timing of addition of BE in the method of the present invention. (A) in FIG. 1 is one example of a change in temperature in a two-step reaction method. (B) in FIG. 1 is one example of a change in temperature of an intermediate method between a two-step reaction method and a BE instantaneous continuous reaction method. (C) in FIG. 1 is one example of a change in temperature in a BE instantaneous continuous reaction method.
Figure 2:
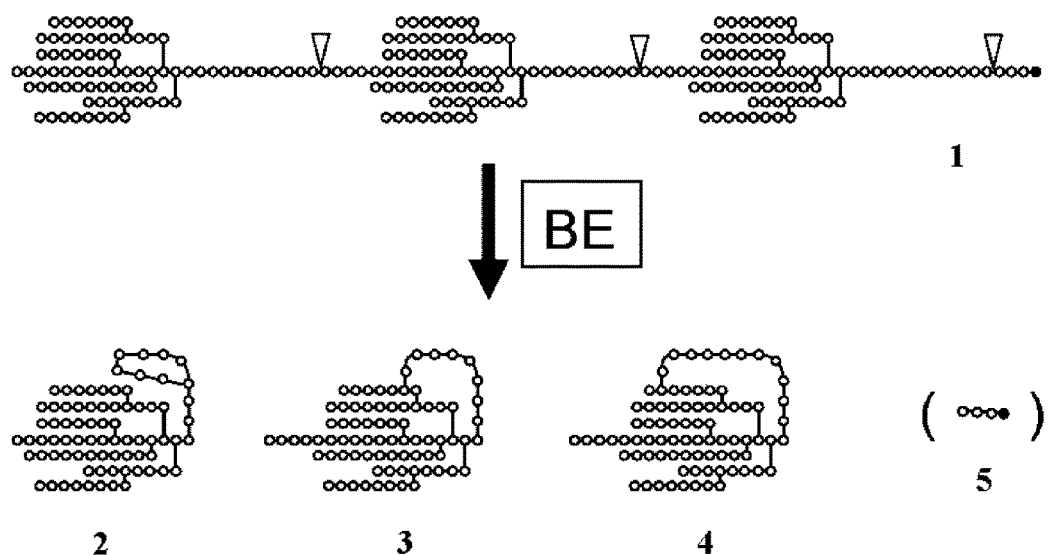
FIG. 2 shows a schematic view of generation of a cyclic-structure-containing branched glucan by BE.

The present invention will be explained in detail below.
1. Material
In the method of the present invention, starch granules, which are a substrate, and a branching enzyme are used.
1.1 Starch Granules
In the present specification, the term "starch granules" refers to starch molecules in a crystal structure. The starch granules may be untreated starch granules, or may be starch granules obtained by chemically modifying or physically treating untreated starch granules. When it is preferable to use an enzymatically treated starch which is classified as a food, the starch granules to be used are representatively untreated starch granules obtained from a plant, and an example thereof includes, but is not limited to, a starch granule which has not undergone a gelatinization process. Alternatively, as a starch granule used in the present invention, a starch granule having such a property that, when it is suspended in water and the suspension is heated, the starch granule is ruptured such that the suspension loses flowability can be used. The starch granules to be used in the present invention have preferably a high amylopectin content.

Plants store starch molecules as granules (i.e., as a large crystal) in amyloplasts. The granules are called starch granules. In the starch granules, starch molecules are mutually bonded through a hydrogen bond or the like. Therefore, starch granules are not easily dissolved in water as they are, and are not also easily digested. When the starch granules are heated together with water, they are swollen and molecules are disentangled to form a colloid. This change is called "gelatinization". The size and shape of the starch granules vary depending on plants from which the starch granules are obtained. In the present invention, commercially available starch granules can be used. Starch granules may be prepared by the method of, for example, purifying starch granules from plants or the like and used in the present invention.

In the present specification, the term "starch" refers to a mixture of amylose and amylopectin. For the starch to be used in the present invention, starch having a high amylopectin content is most preferable. The ratio of amylose and amylopectin contained in starch is different depending on the kind of a plant which produces starch. Most part of starches contained in glutinous rice, glutinous corn or the like is amylopectin. On the other hand, starch comprising only amylose and not amylopectin is not obtained from a normal plant.

In a state of starch granules, an enzyme hardly acts on starch granules since starch molecules are strongly bonded to each other. In a specific embodiment for obtaining an enzymatically treated starch to be treated as a food, the starch granules used in the present invention are isolated or purified from plants, but have not been subjected to an acid treatment, a chemical modification treatment and a heat treatment. In the present specification, the term "untreated" starch granules refer to starch granules which are naturally produced and have not been subjected to a treatment other than treatments required to separate starch granules from other components (for example, protein, lipid and the like) coexisting in a natural state. Accordingly, the respective steps in the method of preparing starch granules, such as the step of removing impurities from plants or the like to purify a starch is not encompassed in a treatment of starch granules in the present specification. It is possible to use, as starch granules, any starch granules as long as they are usually commercially available starch granules.

The starch granules to be used in the present invention are starch which has not been subjected to gelatinization treatment. The starch granules to be used in the present invention retain at least a part of a natural crystal structure, and are difficult to be acted upon by an enzyme. The starch granules to be used in the present invention is preferably such that when, for example, the starch granules are added to water at 30° C. to prepare a 40% by weight water suspension, the suspension are heated at 100° C. for 10 minutes, and thereafter, the suspension is cooled to 60° C., the obtained solution has no flowability. It is noted that "a solution has no flowability" refers to the case where, for example, when 50 g of a solution which has been heated for 10 minutes (60° C.) is placed in a glass beaker having a capacity of 100 ml, the beaker is inverted, and maintained at 60° C. for 1 minute while the beaker is open at the section beneath the sample solution, 20% by weight or more (i.e., 10 g or more) of the placed solution remains in the beaker. When a solution has no flowability, it is difficult to uniformly diffuse an enzyme in the solution. In the present specification, "a solution has flowability" refers to the case where, for example, when a solution is placed in a glass beaker having a capacity of 100 ml, and the beaker is inverted, 80% or more of the total solution is flown down within 1 minute due to the gravity. In the case of a solution in this state, starch can be uniformly dispersed in the solution by adding an enzyme and stirring the mixture. A solution having flowability does not clog a production line used for a normal dextrin production step.

In another specific embodiment, the starch granules used in the present invention may be starch granules treated by subjecting untreated starch granules to a chemical modification or a physical treatment. Examples of the chemically modified starch granules include an acetylated distarch adipate, an acetylated oxidized starch, an acetylated distarch phosphate, a starch sodium octenyl succinate, a starch acetate, an oxidized starch, a bleached starch, a hydroxypropyl distarch phosphate, a hydroxypropyl starch, a distarch phosphate, a monostarch phosphate, and a phosphated distarch phosphate. The "acetylated distarch adipate" refers to those obtained by esterifying a starch with acetic anhydride and adipic anhydride. The "acetylated oxidized starch" refers to those obtained by treating a starch with sodium hypochlorite and then esterifying it with acetic anhydride. The "acetylated distarch phosphate" refers to those obtained by esterifying a starch with sodium trimetaphosphate or phosphorus oxychloride and acetic anhydride or vinyl acetate. The "starch sodium octenyl succinate" refers to those obtained by esterifying a starch with octenyl succinic anhydride. The "starch acetate" refers to those obtained by esterifying a starch with acetic anhydride or vinyl acetate. The "oxidized starch" refers to those obtained by treating a starch with sodium hypochlorite, wherein the content of carboxyl groups is 1.1% or less when carboxyl groups (also referred to as carboxyl groups) in a sample starch are analyzed in accordance with the method for the purity test described in Ministry of Health and Welfare Notification No. 485. Provided that, even when the amount of a carboxyl group is within the above range, the "bleached starch" is not included in the definition of the "oxidized starch". The "bleached starch" refers to those obtained by treating a starch with sodium hypochlorite, wherein the content of carboxyl groups is 0.1% or less when carboxyl groups in a sample starch are analyzed in accordance with the method for the purity test described in Ministry of Health and Welfare Notification No. 485, and wherein the test results of "Confirmation test (3)" of the oxidized starch described in Ministry of Health and Welfare Notification No. 485 are negative and wherein it can be reasonably explained that a change in properties, such as viscosity, of the starch is not caused by oxidation. Those in which, even if the amount of carboxyl groups is 0.1% or less, properties such as viscosity of the starch change from those of the native starch are classified as the oxidized starch, and are not dealt as a food in Japan but dealt as food additives. The "hydroxypropyl distarch phosphate" refers to those obtained by esterifying a starch with sodium trimetaphosphate or phosphorus oxychloride and etherifying it with propylene oxide. The "hydroxypropyl starch" refers to those obtained by etherifying a starch with propylene oxide. The "distarch phosphate" refers to those obtained by esterifying a starch with sodium trimetaphosphate or phosphorus oxychloride. The "monostarch phosphate" refers to those obtained by esterifying a starch with orthophosphoric acid, a potassium salt or a sodium salt thereof, or sodium tripolyphosphate. The "phosphated distarch phosphate" refers to those obtained by esterifying a starch with orthophosphoric acid, a potassium salt or a sodium salt thereof, or sodium tripolyphosphate, and esterifying it with sodium trimetaphosphate or phosphorus oxychloride.

Examples of the types of the physically treated starch granules include a heat-moisture-treated starch and a thermally inhibited starch.

The starch granules to be used in the present invention may be either an aboveground starch or an underground starch. Examples of the underground starch include a cassaya starch, a potato starch, a sweet potato starch, a kudzu starch, a bracken starch and the like. Examples of the aboveground starch include a wheat starch, a corn starch (for example, a high amylose corn starch, a normal corn starch, and a waxy corn starch), a rice starch (for example, a glutinous rice starch and a nonglutinous rice starch), a bean starch (for example, a green gram starch, a pea starch, an adzuki bean starch, and a fava bean starch), an *Amaranthus* starch and the like. Alternatively, the starch granules may be, for example, starch granules obtained as a byproduct remaining after separation of a main ingredient glucomannan, like konjac root starch. The starch granule to be used in the present invention is preferably a glutinous corn starch such as waxy corn starch or a glutinous rice starch. In another embodiment, the starch granules to be used in the present invention are tapioca starch, potato starch or normal corn starch. An amylopectin content in the starch granules is generally about 40% by weight to about 100% by weight. When the amylopectin content in the starch granules is about 50% by weight or more, particularly about 60% by weight or more, the method of the present invention is particularly suitably used. In the case where the chemically modified starch is used as the starch granules, it is preferred to use an acetylated distarch adipate, an acetylated oxidized starch, an acetylated distarch phosphate, a starch sodium octenyl succinate, a starch acetate, an oxidized starch, a bleached starch, a hydroxypropyl distarch phosphate, a hydroxypropyl starch, a distarch phosphate, a monostarch phosphate or a phosphated distarch phosphate of a glutinous corn, a glutinous rice starch, a cassaya starch, a potato starch or a normal corn starch. In the case where the physically treated starch is used, it is preferred to use a heat-moisture-treated starch or a thermally inhibited starch of a glutinous corn starch, a glutinous rice starch, a cassaya starch, a potato starch or a normal corn starch.

The average degree of polymerization of the starch to be used in the present invention is preferably about $1 \times 10^3$ or more, more preferably about $5 \times 10^3$ or more, further preferably about $1 \times 10^4$ or more, and most preferably about $2 \times 10^4$ or more. The average degree of polymerization of the starch to be used in the present invention is preferably about $1 \times 10^7$ or less, more preferably about $3 \times 10^6$ or less, further preferably about $1 \times 10^6$ or less, and most preferably about $3 \times 10^5$ or less.

It is preferable that the starch granules to be used in the present invention contains impurities as little as possible. The content of impurities in starch granules to be used as a raw material is preferably about 10% by weight or less, more preferably about 5% by weight or less, and further preferable about 1% by weight or less.

1.2 Branching Enzyme

A branching enzyme (systematic name: 1,4-α-D-glucan: 1,4-α-D-glucan 6-α-D-(1,4-α-D-glucano)-transferase, EC 2.4.1.18; also described as BE in the present specification) is an enzyme which cleaves α-1,4-glucosidic bonds and transfers the bond to an OH group at the 6-position of another glucosyl residue to form α-1,6-glucosidic bond. BE is also referred to as 1,4-α-glucan branching enzyme, a branching enzyme or a Q enzyme in the art. BE is distributed widely in animals, plants, mould fungi, yeasts and bacteria, and catalyses synthesis of a branched bond of glycogen or starch.

The BE is preferably a heat-resistant BE. The heat-resistant BE refers to a BE having an optimum reaction temperature of 45° C. or higher.

The branching enzyme activity is typically measured as decrease in the absorbance of an amylose-iodine complex at 660 nm and is based on the function of BE to cleave α-1,4-glucosidic bonds and transfer the bond to an OH group on the 6-position of another glucosyl residue thereby forming α-1,6-glucosidic bonds to reduce a linear-chain moiety of amylose.

Methods of measuring the branching enzyme activity of BE are known in the art and described, for example, in Takata, H. et al., J. Appl. Glycosci., 2003. 50: p. 15-20. The branching enzyme activity of a BE is measured for example as follows: First, 50 μL of enzyme solution is added to 50 μL of substrate solution (0.12% (w/v) amylose (Type III, manufactured by Sigma Chemical)) to initiate the reaction. The reaction is carried out at the optimum reaction temperature of the BE. After the BE is allowed to act for 10 minutes, 1 mL of 0.4 mM hydrochloric acid solution is added to terminate the reaction. Thereafter, 1 mL of iodine solution is added to, and mixed well, then the reaction mixture is measured for its absorbance at 660 nm. As a control solution, the solution to which the 0.4 mM hydrochloric acid solution is added before addition of the enzyme solution is simultaneously prepared. The substrate solution is prepared by adding 200 μL of 50 mM potassium phosphate buffer (pH 7.5) to 100 μL of 1.2% (w/v) amylose type III solution (dissolved in dimethyl sulfoxide), then adding 700 μL distilled water thereto, and mixing the resulting mixture well. Provided that the pH of the buffer is adjusted to the optimum reaction pH of the BE used. The iodine solution is prepared by mixing 0.5 mL of 1 N hydrochloric acid with 0.125 mL of stock solution (2.6% by weight of $I_2$, 26% by weight of KI aqueous solution) and adjusting the volume of the mixture to 65 mL with distilled water. The BE activity of the enzyme solution is calculated according to the following equation:

BE activity (unit (U)/mL)={[(absorbance of control solution at 660 nm)−(absorbance of sample solution at 660 nm)]/(absorbance of control solution at 660 nm)}×100×1/10×1000/50    Equation 1

From this BE activity, the BE activity per 1 g of a substrate can be calculated.

In this specification, in principle, the BE activity calculated in accordance with the aforementioned equation is used as the activity of the BE. Accordingly, when it is simply referred as "activity", it represents "BE activity" calculated in accordance with the aforementioned equation, and when it is simply referred as "unit" or "U", it means "unit" or "U" in BE activity calculated in accordance with the aforementioned equation.

The optimum reaction temperature of BE is preferably about 45° C. or more and about 90° C. or less. In this specification, the "optimum reaction temperature" refers to the temperature at which the BE activity is the highest when the aforementioned measurement of the BE activity is conducted by varying only the temperatures. The optimum reaction temperature is preferably about 45° C. or more, about 50° C. or more, more preferably about 55° C. or more, particularly preferably about 60° C. or more, and most preferably about 65° C. or more. There is no upper limit of the preferable optimum reaction temperature. However, the optimum reaction temperature of an actual BE has an upper limit, and may be, for example, about 90° C. or less, about 85° C. or less, about 80° C. or less, about 75° C. or less, or the like.

In the method of the present invention, it is preferable that the BE has a branching enzyme activity at a temperature at which the BE allowed to act on the starch granule. For example, when a reaction is performed at 85° C., it is preferable that the BE has a branching enzyme activity at 85° C., when a reaction is performed at 90° C., it is preferable that the BE has a branching enzyme activity at 90° C., when a reaction is performed at 95° C., it is preferable that the BE has a branching enzyme activity at 95° C., and when a reaction is performed at 100° C., it is preferable that the BE has a branching enzyme activity at 100° C.

In this case, "has a branching enzyme activity" at a specified temperature refers to the fact that, when measurement is performed in the same manner as in the aforementioned measurement of the branching enzyme activity except that the BE is allowed to act at the specified temperature, the BE activity is detected. When used in the present invention, the BE activity in a mixed liquid at a temperature at which a branching enzyme is allowed to act is preferably about 10 U/mL or more, more preferably about 20 U/mL or more, further preferably about 30 U/mL or more, particularly preferably about 40 U/mL or more, and most preferably about 50 U/mL or more. As far as aggregation of BE due to thermal denaturation is not extremely large, the higher BE activity at this specified temperature is preferable, has no particular upper limit, and may be, for example, 10,000,000 U/mL or less, 1,000,000 U/mL or less, 100,000 U/mL or less, 10,000 U/mL or less, 1,000 U/mL or less, and the like.

The BE is preferably derived from a bacterium belonging to the genus *Aquifex*, the genus *Rhodothermus*, the genus *Bacillus*, or the genus *Thermosynechococcus*. The BE is preferably derived from a bacterium belonging to the genus *Escherichia*. The BE is preferably derived from a bacterium belonging to the genus *Anaerobranca*. The BE is preferably derived from a bacterium belonging to the genus *Deinococcus*.

The BE is more preferably derived from a bacterium selected from the group consisting of *Aquifex aeolicus*, *Aquifex pyrophilus*, *Rhodothermus obamensis*, *Rhodothermus marinus*, *Bacillus stearothermophilus*, *Bacillus caldovelox*, *Bacillus thermocatenulatus*, *Bacillus caldolyticus*, *Bacillus flavothermus*, *Bacillus acidocaldarius*, *Bacillus caldotenax*, *Bacillus smithii*, *Thermosynechococcus elongatus* and *Escherichia coli*; further more preferably derived from a bacterium selected from the group consisting of *Aquifex aeolicus*, *Rhodothermus obamensis*, *Bacillus stearothermophilus*, *Bacillus caldovelox*, *Bacillus thermocatenulatus*, *Bacillus caldolyticus* and *Escherichia coli*; and most preferably derived from *Aquifex aeolicus* or *Rhodothermus obamensis*. It is noted that, recently, a thermophilic bacterium in genus *Bacillus* is often described as a bacterium in genus *Geobacillus*. For example, *Bacillus stearothermophilus* refers to the same bacterium as *Geobacillus stearothermophilus*.

In the present specification, an enzyme "derived from" an organism, means not only that the enzyme is directly isolated from the organism, but also refers to an enzyme obtained by utilizing the organism in any form. For example, when a gene encoding an enzyme obtained from an organism is introduced into *Escherichia coli*, and the enzyme is isolated from that *Escherichia coli*, the enzyme is referred to as being "derived from" the organism.

In the present specification, "identity" of a sequence (for example, an amino acid sequence, a base sequence and the like) refers to the degree of occurrence of the same amino acid (base when base sequences are compared) between two sequences. Identity can be generally determined by comparing two amino acid sequences or two base sequences, and comparing these two sequences which are aligned in an optimal format, which can contain additions or deletions.

In the present specification, the identity of sequences is calculated using maximum matching of GENETYX-WIN Ver.4.0 (Genetics Co., Ltd.). This program aligns sequence data to be analyzed, and sequence data to be compared so that amino acid pairs matched between sequences become greatest while substitution and deletion are considered, and thereupon, gives a score to each of Matches, Mismatches, and Gaps, calculates a sum, outputs alignment at the smallest sum, and calculates identity thereupon (Reference: Takeishi, K., and Gotoh, O. 1984. Sequence Relationships among Various 4.5 S RNA Species J. Biochem. 92:1173-1177).

The base sequence encoding wild type BE from *Aquifex aeolicus* VF5 is shown in SEQ ID NO: 1, and the amino acid sequence thereof is shown in SEQ ID NO: 2. In this specification, the "wild type" BE encompasses not only BE isolated from a bacterium originally producing BE, but also BE obtained by genetic recombination, having the same amino acid sequence as that of the wild type BE. The method of cloning the base sequence encoding the wild type BE derived from *Aquifex aeolicus* VF5 is described in Takata, H. et al, J. Appl. Glycosci., 2003. 50: p. 15-20 and van der Maarel, M. J. E. C. et al., *Biocatalysis and Biotransformation,* 2003, Vol. 21, pp. 199-207.

The base sequence encoding wild type BE from *Rhodothermus obamensis* JCM9785 is shown in SEQ ID NO: 3, and the amino acid sequence thereof is shown in SEQ ID NO: 4. The method of cloning the base sequence encoding wild type BE derived from *Rhodothermus obamensis* JCM9785 is described in Shinohara, M. L. et al, Appl Microbiol Biotechnol, 2001. 57(5-6): p. 653-9 and Japanese National Phase PCT Laid-Open Publication No. 2002-539822.

The base sequences and amino acid sequences of these wild type BEs are illustrative, and it is known that variants having a slightly different sequence from these sequences can occur naturally. Such naturally occurring variants and variants created by artificially mutating the wild type BEs, in addition to the BEs having these exemplary sequences, can be used in the method of the present invention insofar as they have BE activity. For example, the pamphlet WO2000/058445 and Patent Document 3 describe variants of BE derived from *Rhodothermus obamensis*. BE variants preferably have activity equal to, or higher than, that of BE before modification. For example, the amino acid sequence of BE to be used in the present invention, in a certain embodiment, may be identical with (that is, 100% identical with) an amino acid sequence (that is, a reference amino acid sequence) selected from the group consisting of SEQ ID NO: 2 and SEQ ID NO: 4; or this amino acid sequence may, in another embodiment, be altered in up to a certain number of amino acids compared with a reference amino acid sequence. Such alterations can be selected from the group consisting of a deletion, a substitution (including conservative and non-conservative substitution), or an insertion of at least 1 (preferably 1 or several) amino acids. This alteration may occur at a position of an amino terminus or a carboxyl terminus of a reference amino acid sequence, or may occur at any position other than these termini. Alteration of an amino acid residue may be interspersed with one residue, or a few residues may be contiguous. Those skilled in the art can easily select a BE having a desired property. Alternatively, a gene encoding the objective BE may be directly chemically synthesized. Methods for such chemical synthesis are well-known in the art.

In a particular embodiment, the BE to be used in the present invention has an amino acid sequence having preferably about 50% or more, more preferably about 60% or more, further preferably about 70% or more, still further preferably about 80% or more, particularly preferably about 90% or more, and most preferably about 95% or more sequence identity with an amino acid sequence of SEQ ID NO: 2 or SEQ ID NO: 4, and has a BE activity. The BE to be used in the present invention has particularly preferably an amino acid sequence having about 96% or more, about 97% or more, about 98% or more or about 99% or more sequence identity with an amino acid sequence of SEQ ID NO: 2 or SEQ ID NO: 4, and has a BE activity.

The amount of the BE to be used in the method of the present invention is representatively about 100 U/g substrate or more, preferably about 500 U/g substrate or more, and more preferably about 5,000 U/g substrate or more, based on the starch granule (i.e., substrate) in the solution at reaction initiation. The amount of the BE to be used in the method of the present invention is representatively about 500,000 U/g substrate or less, preferably about 100,000 U/g substrate or less, and further preferably about 50,000 U/g substrate or less, based on the starch granule in the solution at reaction initiation. When the used amount of the BE is too large, an enzyme denatured during the reaction may be easily aggregated. When the use amount thereof is too small, the yield of an objective cyclic-structure-containing branched glucan may be reduced.

When the method of the present invention is performed by a two-step reaction method, preferably, the amount of the BE to be used is representatively about 100 U/g substrate or more, preferably about 500 U/g substrate or more, more preferably about 5,000 U/g substrate or more, based on the starch granule (i.e., substrate) in the solution at reaction initiation; the amount of the BE to be used in the method of the present invention is representatively about 500,000 U/g substrate or less, preferably about 100,000 U/g substrate or less, and further preferably about 50,000 U/g substrate or less, based on the starch granule in the solution at reaction initiation.

When the method of the present invention is performed by an instantaneous continuous reaction method, preferably, the amount of the BE which is used initially is representatively about 100 U/g substrate or more, preferably about 500 U/g substrate or more, more preferably about 10,000 U/g substrate or more, based on the starch granule (i.e., substrate) in the solution at reaction initiation; the amount of the BE which is used initially in the method of the present invention is representatively about 500,000 U/g substrate or less, preferably about 200,000 U/g substrate or less, further preferably about 80,000 U/g substrate or less, based on the starch granule in the solution at reaction initiation.

When the method of the present invention is performed by an instantaneous continuous reaction method, and after first addition of the BE, a reaction mixed liquid is cooled to some extent after gelatinization of the starch granule at 85° C. to 130° C. and, thereafter, the BE is added again to act thereon; then the amount of the BE which is used at the second time is representatively about 10 U/g substrate or more, preferably about 100 U/g substrate or more, and more preferably about 500 U/g substrate or more, based on the starch granule (i.e., substrate) in the solution at reaction initiation; and the amount of the BE which is used at the second time in this case is representatively about 500,000 U/g substrate or less, preferably about 50,000 U/g substrate or less, and further preferably about 10,000 U/g substrate or less, based on the starch granule in the solution at reaction initiation.

It is preferable that the enzyme activity of endo-type amylases which hydrolyze an α-1,4-glucosidic bond or an α-1,6-glucosidic bond in starch is not detected, or the activity is extremely low in the enzyme to be used in the present invention, and it is most preferable that the enzyme activity is not detected.

The enzyme to be used in the present invention can be used in a reaction, regardless of a purified enzyme or a crude enzyme, and even if it is an immobilized enzyme, it can be used in a reaction; and the reaction format may be a batch format or a continuous format. As a method of immobilization, a method well-known to a person skilled in the art such as a support binding method (e.g., covalent binding method, ion binding method, or physical adsorption method), a crosslinking method or an inclusion method (lattice-type or microcapsule-type) can be used.

2. Production Method of the Present Invention

The production method of the present invention is a method for producing a cyclic glucan, the method comprising the steps of:

(1) preparing a mixed liquid which comprises a branching enzyme in which starch granules are suspended at a concentration of 5% by weight or more and 50% by weight or less, and allowing the branching enzyme to act on starch in the starch granules, wherein a temperature of the mixed liquid at the time of preparation is 0° C. or higher and not higher than the gelatinization starting temperature of the starch granules; and (2) elevating the temperature of the mixed liquid to 85° C. or higher, and 129° C. or lower, wherein in the method, none of α-amylase, β-amylase, amyloglucosidase and α transglucosidase is added to the mixed liquid.

In the production method of the present invention, first, a reaction mixed liquid is prepared. The reaction mixed liquid can be prepared by, for example, adding a BE and a substrate (i.e., starch granules) to an appropriate solvent. Alternatively, the reaction mixed liquid may be prepared by mixing a solution containing a BE, and a suspension containing a substrate (i.e., starch granules). For example, in the method called "two-step reaction method" in the present specification, the reaction mixed liquid may be prepared by adding a BE to a starch suspension to obtain a mixed liquid, or the reaction mixed liquid may be prepared by mixing a BE, starch granules and a solvent (e.g., water). For example, when production is performed utilizing a facility for the conventional instantaneous continuous reaction method for producing dextrin, the reaction mixed liquid can be formed by supplying a solution containing a BE and a solution containing starch granules through separate pipes, and mixing the solutions by joining them in a pipe.

Any buffer may be added to this reaction mixed liquid for the purpose of adjusting pH, if necessary, as far as an enzymatic reaction is not inhibited. The pH of the reaction mixed liquid can be arbitrarily set as far as the BE used can exert the activity at the pH. It is preferable that the pH of the reaction mixed liquid is around the optimum pH of the BE used. The pH of the reaction mixed liquid is representatively about 2 or higher, preferably about 3 or higher, further preferably about 4 or higher, particularly preferably about 5 or higher, particularly preferably about 6 or higher, and most preferably about 6.5 or higher. The pH of the reaction mixed liquid is representatively about 13 or lower, preferably about 11 or lower, further preferably about 10 or lower, particularly preferably about 9 or lower, particularly preferably about 8 or lower, and most preferably about 7.5 or lower. In one embodiment, the pH of the reaction mixed liquid is representatively within ±3 of the optimum pH of the BE to be used, preferably within ±2 of the optimum pH, further preferably within ±1 of the optimum pH, and most preferably within ±0.5 of the optimum pH.

The temperature of a mixed liquid which comprises a branching enzyme in which starch granules are suspended at a concentration of 5% by weight or more and 50% by weight or less, at the preparation of this mixed liquid, is 0° C. or higher and not higher than the gelatinization starting temperature of the starch. The gelatinization starting temperature of the starch can vary depending on a plant from which the starch granule to be used is obtained, when the plant is harvested, the place where the plant was cultivated, or the like. Generally, the gelatinization starting temperature of normal corn starch is about 70.7° C., the gelatinization starting temperature of waxy corn starch (i.e., glutinous corn starch) is about 67.5° C., the gelatinization starting temperature of rice starch is about 73.5° C., the gelatinization starting temperature of potato starch is about 62.6° C., the gelatinization starting temperature of tapioca starch is about 68.4° C., and the gelatinization starting temperature of green gram starch is about 71.0° C.

The gelatinization starting temperature of the starch can be measured by amylograph. A method of measuring the gelatinization starting temperature is described in "Denpun kagaku no jiten (Dictionary of Starch Science)", page 194 to page 197.

The temperature of a mixed liquid which comprises a branching enzyme in which starch granules are suspended at a concentration of 5% by weight or more and 50% by weight or less, at the preparation of this mixed liquid, can vary so that the temperature is appropriate to the starch granules to be used, and the temperature is, for example, about 0° C. or higher, preferably about 10° C. or higher, further preferably about 15° C. or higher, particularly preferably about 20° C. or higher, and most preferably about 25° C. or higher. The temperature of a mixed liquid which comprises a branching enzyme in which starch granules are suspended at a concentration of 5% by weight or more and 50% by weight or less, at the preparation of this mixed liquid, can vary so that the temperature is appropriate to the starch granules to be used, and the temperature is, for example, about 67.5° C. or lower, preferably about 60° C. or lower, further preferably about 50° C. or lower, particularly preferably about 40° C. or lower, and most preferably about 35° C. or lower.

When a mixed liquid containing the BE and the starch granules is prepared, the BE acts on the starch granules, and the starch granules are gradually degraded. The temperature of the mixed liquid containing the BE and the starch granule may be (1) about 75° C. or lower for a predetermined period of time before temperature raising, or (2) may be raised immediately to a high temperature (e.g., a temperature of about 80° C. or higher or about 85° C. or higher, and about 129° C. or lower). When the reaction is allowed to proceed by adjusting it at a temperature of about 75° C. or lower for a predetermined period of time before temperature raising, the amount of the BE may be slightly smaller. When the temperature is raised immediately to a high temperature (e.g., a temperature of about 80° C. or higher or about 85° C. or higher, and about 129° C. or lower), a period of time during which the BE acts is shortened, and thus, it is preferable that the amount of the BE to be used is increased based on the amount of the starch granules. The case of (1) is referred to as "BE two-step reaction method", and the case of (2) is referred to as "BE instantaneous continuous reaction method".

In the case of the "BE two-step reaction method", the reaction is performed at a temperature higher than the temperature at the preparation of the mixed liquid, and about 75° C. or lower. The temperature upon this reaction is preferably about 30° C. or higher, more preferably about 35° C. or higher, further preferably about 40° C. or higher, particularly preferably about 45° C. or higher, and most preferably about 50° C. or higher. The temperature during this reaction may be about 75° C. or lower, and for example, can be about 70° C. or lower, about 65° C. or lower, about 60° C. or lower, about 55° C. or lower, about 55° C. or lower, about 50° C. or lower, or the like. In addition, the temperature during this reaction may be a constant temperature, or may be elevated gradually.

In the case of the "BE two-step reaction method", the period of time from the time point of addition of the first BE to a time point of temperature raised to the high temperature (e.g., about 80° C. or higher or about 85° C. or higher, and about 129° C. or lower) (reaction time) is arbitrarily selected. This reaction time can be, for example, about 1 second or longer, about 10 seconds or longer, about 1 minute or longer, about 5 minutes or longer, about 10 minutes or longer, about 20 minutes or longer, about 30 minutes or longer, about 40 minutes or longer, about 50 minutes or longer, or about 1 hour or longer. This reaction time can be, for example, about 72 hours or shorter, about 60 hours or shorter, about 48 hours or shorter, about 36 hours or shorter, about 30 hours or shorter, about 24 hours or shorter, about 12 hours or shorter, about 8 hours or shorter, or about 6 hours or shorter. Within the period of time that is arbitrarily selected, the BE may be further added. In a particular embodiment, for example, both reactions of (1) and (2) may be performed in a tank. In another particular embodiment, for example, the reaction of (1) may be performed in a tank and only the temperature raising reaction of (2) may be performed in a jet cooker.

In the case of the "BE instantaneous continuous reaction method", after preparation of a mixed liquid, a temperature is raised to a high temperature (e.g., a temperature of about 80° C. or higher or about 85° C. or higher, and about 129° C. or lower) in an extremely short period of time. The period of time necessary for completion of raising temperature to a desired temperature after preparation of a mixed liquid may be, for example, about 1 second or longer, about 2 seconds or longer, about 3 seconds or longer, about 4 seconds or longer, or about 5 seconds or longer and, for example, may be about 60 seconds or shorter, about 50 seconds or shorter, about 40 seconds or shorter, about 30 seconds or shorter or about 20 seconds or shorter.

In the method of the present invention, after preparation of a mixed liquid, the temperature of the mixed liquid is raised to a high temperature (e.g., a temperature of about 80° C. or higher or about 85° C. or higher, and about 129° C. or lower). Also at this temperature, the BE acts on the starch in the starch granules, and degrades the starch granules. Further, at this temperature, since the starch is completely gelatinized, the BE becomes more easily to act on the starch. However, when the reaction temperature is higher, the BE is more easily inactivated, and thus, it is preferable to use a BE having high heat resistance.

It is preferable that the raised temperature is about 80° C. or higher or about 85° C. or higher, and 129° C. or lower. The raised temperature can be, for example, about 80° C. or higher, about 81° C. or higher, about 82° C. or higher, about 83° C. or higher, about 84° C. or higher, about 85° C. or higher, about 86° C. or higher, about 87° C. or higher, about 88° C. or higher, about 89° C. or higher, about 90° C. or higher, about 95° C. or higher, or about 100° C. or higher. The raised temperature is preferably about 125° C. or lower, further preferably about 120° C. or lower, still further preferably about 115° C. or lower, particularly preferably about 110° C. or lower, and most preferably about 105° C. or lower. When the raised temperature is higher than 90° C., the ratio of an inactivated BE is increased, and thus, it is preferable to further add an enzyme at this stage. Moreover, when the raised temperature exceeds 100° C., it is necessary that an apparatus has a pressure-resistant structure. Further, when the raised temperature is too high, for example, at 130° C. or higher, thermal degradation of a glucan chain may occur. When the raised temperature is too low, the reaction efficacy is easily reduced, and the yield is easily reduced.

In the "BE two-step reaction method", at a first step, while the starch granules are dissolved little by little, the starch granule is degraded into a cluster unit by the cyclization reaction of BE, and this is continued for some extent of time to make the starch granule smaller. Since the yield is not increased only by this step, it is preferable that a temperature is raised midway to dissolve the starch, and the whole starch is degraded into a cluster unit. By doing so, since the starch has been partially degraded, and the molecular weight thereof has become smaller (due to decrease in amount), the starch solution can retain flowability at the time of raising temperature.

As described above, in the present invention, the "BE instantaneous continuous reaction method" may be performed. In such an embodiment, the method of the present invention can be performed using the same facility as that of the "instantaneous continuous reaction method". The conventional "instantaneous continuous reaction method" is a method adopted for partially degrading raw starch with amylase to industrially produce dextrin having a different molecular weight distribution. In this method, after two liquids of a starch suspension (e.g., about 30° C.) and an amylase solution (e.g., about 30° C.) are mixed in a pipe, the mixed liquid and high pressure steam are further mixed in the pipe, and thus, a temperature can be raised to 100° C. or higher in a retention time of around 10 seconds after enzyme mixing. Thereafter, the temperature of this mixed liquid is raised to about 120° C. to completely dissolve the starch, the solution is then released under the atmospheric pressure, and the temperature is lowered to around 100° C. and, thereafter, the temperature is lowered to about 70° C. with a heat exchanger. In this method, since the temperature is raised to 120° C. or higher within an extremely short period of time, an enzymatic reaction is initiated at the same time with the initiation of dissolution of the starch by charging of steam, and enzyme inactivation occurs in around a few seconds, and thus, there is an advantage that the degree (i.e., molecular weight of dextrin) of partial hydrolysis can be strictly controlled by the added amount of amylase. However, when the starch suspension is heated in this facility without adding amylase, the starch suspension would lose flowability, and would clog the pipe.

On the other hand, in the method of the present invention, unexpectedly, the starch suspension can retain flowability and the problem that the starch clogs a pipe can be avoided by using a BE in place of amylase. In order to increase the reaction efficacy in the present invention, it is necessary to lower the liquid temperature after completion of the temperature raising step, and to add a branching enzyme again, but a merit that the existing production line can be utilized is also great. In the present invention, when the BE instantaneous continuous reaction method is performed, it is preferable that the temperature of the reaction mixed liquid is raised to a high temperature (e.g., a temperature of about 80° C. or higher or about 85° C. or higher, and about 129° C. or lower) to allow gelatinization of the starch and the action of BE, and after that, the temperature of the reaction mixed liquid is lowered to a temperature at which the BE can act (e.g., about 100° C. or lower, about 90° C. or lower, about 80° C. or lower, or about 75° C. or lower), and a BE is further added to make the BE act on the starch.

When a BE is further added in the BE instantaneous continuous reaction method, the production method of the present invention can be, for example, as follows:

a method for producing a cyclic-structure-containing branched glucan, comprising the steps of:

(1) preparing a mixed liquid which comprises a BE in which starch granules are suspended at a concentration of 5% by weight or more and 50% by weight or less, and allowing the BE to act on starch in the starch granules, wherein a temperature of the mixed liquid at the time of preparation is 0° C. or higher and not higher than the gelatinization starting temperature of the starch granule;

(2) elevating the temperature of the mixed liquid to a high temperature (e.g., about 80° C. or higher, about 85° C. or higher or about 95° C. or higher, and 129° C. or lower), for example, in a period of time of about 60 seconds or shorter; and (3) lowering the temperature of the mixed liquid to a temperature at which the BE can act (e.g., about 100° C. or lower, about 90° C. or lower, about 80° C. or lower, or about 75° C., or the like), and further adding a BE to allow the BE to act on the starch.

An example of a change in temperature of a reaction mixed liquid and timing of addition of BE in the method of the present invention is shown in FIG. 1. (A) in FIG. 1 is one example of a change in temperature in a two-step reaction method. (B) in FIG. 1 is one example of a change in temperature of an intermediate method between a two-step reaction method and a BE instantaneous continuous reaction method. (C) in FIG. 1 is one example of a change in temperature of a BE instantaneous continuous reaction method.

The "BE two-step reaction method" and "BE instantaneous continuous reaction method" of the present invention are in common that the BE is added at the gelatinization starting temperature or lower and, thereafter, the temperature is raised. It is also common that each of them is an invention for avoiding the problem that the starch solution loses flowability after the temperature raising.

In the method of the present invention, it is preferable that the reaction mixed liquid maintains flowability in any step.

A product obtained in the method of the present invention is a product having a branching frequency and a weight-average degree of polymerization as described in the following "4. Cyclic-structure-containing branched glucan obtained by the method of the present invention".

The reaction time throughout the entire of the method of the present invention can be determined at an arbitrary period of time, in view of the reaction temperature, the starch concentration in the reaction liquid, the molecular weight of an α-glucan produced by the reaction and the remaining activity of the enzyme. The reaction time can be, for example, about 1 hour or longer, about 2 hours or longer, about 5 hours or longer, about 10 hours or longer, about 12 hours or longer, or about 24 hours or longer. The reaction time has no particular upper limit, but is preferably about 100 hours or shorter, more preferably about 72 hours or shorter, further more preferably about 36 hours or shorter, and most preferably about 24 hours or shorter. It is noted that the "reaction time" throughout the entire method of the present invention is a period of the time from addition of the first BE to completion of the reaction. In the case of the continuous production format, the reaction time is a period of time from the time point of charging raw materials and mixing with the BE, to the time point of outputting a reaction mixed liquid after the reaction.

In the method of the present invention, an enzyme which acts on a glucan chain to generate a byproduct having a reducing end (in the present specification, also referred to as "reducing end generating enzyme") must not be added to the reaction mixed liquid. Examples of the reducing end generating enzyme include α-amylase, (β-amylase, glucoamylase, amyloglucosidase, α-glucosidase, dextrinase, pullulanase, neopullulanase, isoamylase, glycogen debranching enzyme and the like. This is because, by these enzymes, starch or a cyclic-structure-containing branched glucan as a product would be degraded, or a linear glucan having a reducing end would be generated. Further, it is preferable that a cyclodextrin-generating enzyme is not also added in the method of the present invention. This is because when the cyclodextrin-generating enzyme is present, a cyclic structure having a low molecular weight would be generated, and the reaction efficacy would be reduced. Further, this is because when the cyclodextrin-generating enzyme is present, a branched glucan having a cyclic structure not containing an α-1,6-bond would be generated, and it would become extremely difficult to separate this branched glucan from a branched glucan having a cyclic structure containing an α-1,6-bond, which is an object of the present application.

Heating may be performed using any means, but it is preferable to perform heating while stirring is performed, so that heat is uniformly transmitted to the entire of the reaction mixed liquid. The reaction mixed liquid is stirred, for example, by placing into a stainless reaction tank equipped with a warm water jacket and a stirring device.

In addition, in the method of the present invention, at a stage at which the reaction has progressed to some extent, a BE may be further added to the reaction mixed liquid.

In this way, a solution containing a cyclic-structure-containing branched glucan is produced. In the method of the present invention, insolubles may be removed after completion of the reaction. After the completion of the reaction, the reaction mixed liquid may be heated, for example, at 100° C. for 10 minutes, or at a temperature higher than 100° C., or for a period of time longer than 10 minutes, if necessary, and thus an enzyme in the reaction mixed liquid may be inactivated. Alternatively, a subsequent step may be performed without performing treatment of inactivating an enzyme. The reaction mixed liquid may be preserved as it is, or may be treated for isolating the cyclic-structure-containing branched glucan produced.

The method of the present invention is suitable for production at an industrial scale, and is particularly suitable in industrial production using piping installations. The industrial scale refers to that the weight of the starch granules used as a substrate is about 100 kg or more per one batch in the case of a batch format, and is about 5 kg or more per 1 minute in the case of a continuous production format.

The production scale in the case of a batch format is such that the weight of the starch granules used as a substrate can be, for example, about 200 kg or more, about 500 kg or more, about 800 kg or more, about 1 ton or more, about 2 tons or more, about 3 tons or more, about 4 tons or more, about 5 tons or more, or the like, per one batch. The production scale has no particular upper limit. For example, the weight of the starch granules used as a substrate can be, for example, about 1,000 tons or less, about 200 tons or less, about 50 tons or less, about 20 tons or less, about 10 tons or less, about 9 tons or less, about 8 tons or less, about 7 tons or less, about 6 tons or less, or the like, per one batch.

In the case of a continuous production format, the weight of the starch granules used as a substrate can be, for example, about 10 kg or more, about 50 kg or more, about 100 kg or more, about 500 kg or more, or the like, per 1 minute. The production scale has no particular upper limit. For example, the weight of the starch granules used as a substrate can be, for example, about 10 ton or less, about 5 ton or less, about 3 ton or less, about 2 ton or less, about 1 ton or less, about 900 kg or less, about 800 kg or less, about 700 kg or less, about 600 kg or less, or the like, per 1 minute.

The production method of the present invention can be suitably applied to such a large scale facility.

3. Purification of Cyclic-structure-containing Branched Glucan

The produced cyclic-structure-containing branched glucan can be purified as necessary. Examples of the impurities removed by purification include a glucan insoluble in water, BE, inorganic salts and the like. Examples of a method of purifying a glucan include a method using an organic solvent (T. J. Schoch et al., J. American Chemical Society, 64, 2957 (1942)) and a method not using an organic solvent.

Examples of the organic solvent which can be used in purification using the organic solvent include acetone, n-amyl alcohol, pentazole, n-propyl alcohol, n-hexyl alcohol, 2-ethyl-1-butanol, 2-ethyl-1-hexanol, lauryl alcohol, cyclohexanol, n-butyl alcohol, 3-pentanol, 4-methyl-2-pentanol, d,l-borneol, α-terpineol, isobutyl alcohol, sec-butyl alcohol, 2-methyl-1-butanol, isoamyl alcohol, tert-amyl alcohol, menthol, methanol, ethanol and ether.

Examples of a purification method not using an organic solvent include a method of removing a glucan insoluble in water, a BE, inorganic salts and the like by, for example, (1) a filtration method using various types of a filtration instrument after addition of various types of a filtration aid or activated charcoal to a reaction solution, (2) a filtration method using various types of a filtration instrument coated with a various types of a filtration aid in advance, (3) a filtration method of combining these filtration methods, (4) membrane fractionation using an ultrafiltration membrane, and (5) a chromatography, without precipitating a cyclic-structure-containing branched glucan dissolved in water, after the production reaction of the cyclic-structure-containing branched glucan. When the filtration is performed, if necessary, a coagulant may be added to a reaction liquid.

Examples of the filtration aid which can be used in purification include diatomaceous earth, perlite, cellulose and the like. Examples of the filtration instrument include a filter press, a decanter-type centrifuge, a vacuum dehydrator, a belt press, a screw press, a multi-disc dehydrator and the like.

Examples of the ultrafiltration membrane which can be used in purification include an ultrafiltration membrane of a molecular weight cut off of about $1\times10^3$ to about $1\times10^4$, preferably about $5\times10^3$ to about $5\times10^4$, more preferably about $1\times10^4$ to about $3\times10^4$ (for example, UF membrane unit manufactured by DAICEL).

Examples of a support which can be used in chromatography include a support for gel filtration chromatography, a support for ligand exchange chromatography, a support for ion-exchange chromatography and a support for hydrophobic chromatography.

In the method of the present invention, the yield of the present glucan from the starch granule as a raw material is very high, and is approximately 100%. In some cases, low-molecular glucans having only a cyclic structure are produced, but these glucans can be easily separated from a cyclic glucan having an objective branch structure, for example, by gel filtration using Sephadex.

In the present specification, the yield is calculated by the following equation:

$$\text{Yield (\% by weight)} = \{(\text{weight of generated cyclic-structure-containing branched glucan (g)})/(\text{weight of starch granules used (g)})\} \times 100$$

4. Cyclic-structure-containing Branched Glucan Obtained by the Method of the Present Invention It is considered that the glucan produced by the method of the present invention has a structure in which a part of the chain of a highly branched glucan forms a cyclic structure. For this reason, the glucan of the present invention is referred to as a "cyclic-structure-containing branched glucan".

The branching frequency of the cyclic-structure-containing branched glucan of the present invention is shown by the ratio of an α-1,6 branching. The ratio of an α-1,6 branching can be, for example, about 2% or more, about 3% or more, about 4% or more, about 5% or more, about 6% or more, about 7% or more, or the like. The ratio of an α-1,6 branching has no upper limit, but the ratio can be, for example, about 25% or less, about 20% or less, about 15% or less, about 10% or less, about 8% or less, or the like.

The branching frequency is calculated by the following equation:

$$\text{Branching frequency (\%)} = \{(\text{number of branching})/(\text{glucose unit number of entire molecule})\} \times 100$$

The molecular weight of the cyclic-structure-containing branched glucan produced by the method of the present invention is preferably about 30000 or more, further preferably about 50000 or more, and particularly preferably about 100000 or more. The molecular weight of the cyclic-structure-containing branched glucan of the present invention is preferably about 500000 or less, further preferably about 300000 or less, and particularly preferably about 200000 or less.

The average degree of polymerization of a cyclic structural moiety of the cyclic-structure-containing branched glucan obtained by the method of the present invention is preferably about 10 or more, more preferably about 15 or more, and further preferably about 20 or more. The average degree of polymerization of a cyclic structural moiety of the cyclic-structure-containing branched glucan obtained by the method of the present invention is preferably about 500 or less, more preferably about 300 or less, and further preferably about 100 or less.

The average degree of polymerization of a branched structural moiety of the cyclic-structure-containing branched glucan obtained by the method of the present invention is preferably about 40 or more, more preferably about 100 or more, further preferably about 300 or more, and further more preferably about 500 or more. The average degree of polymerization of a branched structural moiety of the cyclic-structure-containing branched glucan obtained by the method of the present invention is preferably about $4 \times 10^3$ or less, more preferably about $3 \times 10^3$ or less, further preferably about $2 \times 10^3$ or less, and further more preferably about $1 \times 10^3$ or less.

The number of α-1,6-glucosidic bonds of a cyclic structural moiety of the cyclic-structure-containing branched glucan obtained by the method of the present invention may be at least 1, and can be, for example, 1 or more, 5 or more, 10 or more, or the like; the number of α-1,6-glucosidic bonds of a cyclic structural moiety of the cyclic-structure-containing branched glucan obtained by the method of the present invention can be, for example, about 200 or less, about 50 or less, about 30 or less, about 15 or less, about 10 or less, or the like.

As the cyclic-structure-containing branched glucan obtained by the method of the present invention, a glucan having one kind of degree of polymerization may be used alone, or a mixture of glucans having various degrees of polymerization may be used. Preferably, the degree of polymerization of the cyclic-structure-containing branched glucan obtained by the method of the present invention is such that the ratio of the degree of polymerization ($DP_{max}/DP_{min}$) between a glucan having the greatest degree of polymerization ($DP_{max}$) and a glucan having the minimum degree of polymerization ($DP_{min}$) is about 100 or less, more preferably about 50 or less, and further more preferably about 10 or less.

The cyclic-structure-containing branched glucan obtained by the method of the present invention is preferably such that a part of the branched glucan structure forms a ring. Herein, the cyclic structural moiety is a cyclic structural moiety formed with an α-1,4-glucosidic bond and an α-1,6-glucosidic bond, and the branched structural moiety is a non-cyclic structural moiety bound to the cyclic structural moiety. The degree of polymerization of each unit chain of this branched structural moiety is preferably about 10 or more, and preferably about 20 or less on average.

The average degree of polymerization of the cyclic-structure-containing branched glucan obtained by the method of the present invention is preferably about 50 or more, more preferably about 200 or more, further preferably about 400 or more, and most preferably about 600 or more. The average degree of polymerization of the cyclic-structure-containing branched glucan obtained by the method of the present invention is preferably about $5 \times 10^3$ or less, more preferably about $4 \times 10^3$ or less, further preferably about $3 \times 10^3$ or less, and most preferably about $2 \times 10^3$ or less.

The number of branching in the cyclic-structure-containing branched glucan obtained by the method of the present invention (i.e., the number of α-1,6-glucosidic bonds) is preferably about 2 or more, more preferably about 8 or more, and further preferably about 20 or more. The number of branching of the cyclic-structure-containing branched glucan obtained by the method of the present invention (i.e., the number of α-1,6-glucosidic bonds) is preferably about 800 or less, more preferably about 600 or less, and further preferably about 400 or less.

In the cyclic-structure-containing branched glucan obtained by the present invention, the ratio of the number of α-1,6-glucosidic bonds and the number of α-1,4-glucosidic bonds ("number of α-1,6-glucosidic bonds":"number of α-1,4-glucosidic bonds") is preferably 1:4 to $1:1 \times 10^3$, more preferably 1:5 to $1:1 \times 10^3$, further preferably 1:10 to $1:1 \times 10^3$, and further preferably 1:20 to 1:100.

The α-1,6-glucosidic bonds may be randomly distributed, or may be uniformly distributed in the cyclic-structure-containing branched glucan obtained by the method of the present invention. The distribution to such an extent that a linear part of 5 or more saccharide units is formed in the cyclic-structure-containing branched glucan obtained by the method of the present invention is preferable.

A macromolecule such as a glucan is generally not a uniform molecule, but is a mixture of molecules having various sizes, and thus, its molecular weight is evaluated in terms of a number-average molecular weight (Mn) or a weight-average molecular weight (Mw). The Mn is determined by dividing the total mass of the system by the number of molecules contained in the system. That is, the Mn is an average by number fraction. On the other hand, the Mw is an average by weight fraction. In the case of a completely homogeneous substance, the Mw becomes equal to the Mn, but since a macromolecule generally has a molecular weight distribution, and therefore, the Mw becomes greater than the Mn. Thus, it follows that as Mw/Mn exceeds 1 and becomes higher, a degree of heterogeneity of a molecular weight becomes higher (the molecular weight distribution is broader).

The Mn can be determined by evaluating the number of molecules. That is, in the case of amylose or the like, the Mn can be determined by measuring the number of reducing ends. The number of reducing ends can be determined, for example, by the Modified Park-Johnson method described in Takata, H. et al., Cyclization reaction catalyzed by branching enzyme. J. Bacteriol., 1996. 178: p. 1600-1606. The number of reducing ends can be also determined by the gel filtration chromatography (MALLS method) using both of a differential refractometer in combination with a multi-angle laser-light scattering detector as described in Takata, H. et al., J. Appl. Glycosci., 2003. 50: p. 15-20. The Mw can be determined by the MALLS method described in Takata, H. et al., J. Appl. Glycosci., 2003. 50: p. 15-20.

In the present specification, the molecular weight of a substrate is evaluated mainly in terms of the number-average molecular weight (Mn), while the molecular weight of a product glucan is evaluated mainly in terms of weight-average molecular weight (Mw). This is because, in the product, when a cyclization reaction occurs, the Mn cannot be correctly evaluated by the method of evaluating the number of reducing end. This is also because, when the molecular weight of a very large molecule is evaluated, the number of reducing ends is relatively small, thus making accurate evaluation of the Mn difficulty. This is further because the method of evaluating Mn by the MALLS method is based on the premise that fractionation by gel filtration is complete, so when the fractionation is incomplete, accurate evaluation of Mn is not feasible.

Byproduct

In the glucan produced by the method of the present invention, non-cyclic glucans (i.e., a glucan having a reducing end) which are produced as a byproduct upon production of the glucan are less.

The method of the present invention has an advantage that byproduct is less. For this reason, a preparation product can be obtained without increasing the amount of a reducing end as compared with starch as a starting substance. Originally, starch has the extremely small number of reducing ends thereof, and thus, in the glucan obtained by the method of the present invention, the number of reducing ends thereof is extremely small.

In the present specification, "no reducing power" or "having no reducing power" refers to that the amount of a reducing end is equivalent to that of the starch or less.

More specifically, the amount of a reducing end of a dried preparation product (e.g., glucan-containing powder or glucan purified product) containing the glucan obtained by the method of the present invention is at a detection limit or less when measured according to the Modified Park-Johnson method (Hizukuri et al., Starch, Vol., 35, pp. 348-350 (1983)). Preferably, the amount of a reducing end of this dried preparation product is about 0.01% by weight or less (i.e., a reducing power of 1 kg of dried preparation product is a reducing power of 0.1 g of glucose or less), further preferably about 0.001% by weight or less, and most preferably about 0.0001% by weight or less in terms of a reducing power of glucose.

Confirmation of Possession of Cyclic Structure

The confirmation that the cyclic-structure-containing branched glucan obtained by the production method of the present invention has a cyclic structure can be performed using exo-type glucoamylase.

The exo-type glucoamylase is an enzyme which hydrolyzes an α-1,4-glucosidic bond sequentially from a non-reducing end of a glucan such as starch. It is known that, although a rate is slow, the enzyme can hydrolyze an α-1,6-glucosidic bond from a non-reducing end. Amylose and amylopectin having no cyclic structure are completely degraded to glucose with exo-type glucoamylase. However, in a glucan having a cyclic structure in the molecule, only its non-cyclic structural moiety (i.e., branched structural moiety) is degraded with glucoamylase, and a cyclic structural moiety remains as a substance which does not undergo degradation with glucoamylase (hereinafter, referred to as glucoamylase-resistant component).

Whether this glucoamylase-resistant component (cyclic structural moiety) has an α-1,6-glucosidic bond or not can be determined by sensitivity to a debranching enzyme which cuts an α-1,6-bond.

A cyclic glucan having an α-1,6-glucosidic bond is completely degraded to glucose by using a debranching enzyme and glucoamylase in combination.

On the other hand, a glucan of a cyclic structure having no α-1,6-glucosidic bond (having only an α-1,4-glucosidic bond) is not degraded by using a debranching enzyme and exo-type glucoamylase in combination. This cyclic glucan can be completely degraded to glucose by using endo-type α-amylase and glucoamylase in combination.

By utilizing these properties, it is possible to determine the quantity of a cyclic structural moiety, non-cyclic (branched) structure moiety, and cyclic structural moiety having only α-1,4-glucosidic bond(s) of a glucan.

It can be confirmed by the properties of the following (1) to (6) that the cyclic-structure-containing branched glucan produced by the method of the present invention has a cyclic structure.

(1) The number of reducing ends does not increase as compared with a raw material (starch etc.). That is, a reducing end cannot be detected. The quantity of the number of reducing ends can be determined by the Modified Park-Johnson method of Hizukuri et al., Carbohydr. Res. 94: 205-213 (1981).

(2) When glucoamylase, which is an exo-type amylase, is allowed to act on the glucan, a glucoamylase-resistant component remains. The component is not being degraded even when phosphatase (Sigma) is allowed to act thereon, and then glucoamylase is further allowed to act thereon.

(3) The aforementioned glucoamylase-resistant component is degraded with isoamylase (manufactured by Hayashibara Biochemical Research Institute Co., Ltd.), which hydrolyzes an α-1,6-glucosidic bond in starch, and becomes accessible to the action of glucoamylase.

(4) The aforementioned glucoamylase-resistant component is degraded with endo-type α-amylase (manufactured by Nagase Seikagaku Kogyo Co., Ltd.), which hydrolyzes an α-1,4-glucosidic bond in starch, and becomes accessible to the action of glucoamylase.

(5) Hydrolysis using the endo-type α-amylase of (4) generates isomaltosylmaltose (IMM). This is consistent with the description that minimum limit dextrin, where endo-type α-amylase is allowed to act on glucan having an α-1,6-glucosidic bond, is IMM (Yamamoto, T., Handbook of amylase and related enzymes, Pergamon Press, p 40-45 (1988)).

(6) When the molecular weight of the aforementioned glucoamylase-resistant component is analyzed with a laser ionization TOF-MS apparatus (manufactured by SHIMADZU CORPORATION), the obtained value of the molecular weight is consistent with the theoretical value of a cyclic glucan, and is not consistent with the theoretical value of a non-cyclic glucan.

The detection of the aforementioned glucoamylase-resistant component used for confirming the cyclic structural moiety can be performed as follows. For example, glucoamylase is added to a glucan generated by the aforementioned reaction to react them, for example, at about 40° C. overnight. After this reaction product is heated at 100° C. for 10 minutes, and insolubles are removed by centrifugation, ethanol in a 10-fold amount is added, and the remaining polysaccharide is collected as a precipitate by centrifugation. This operation is repeated once more to obtain a glucoamylase-resistant component, provided that a short period of time (e.g., 1 to 2 hours) is sufficient for the period of time of the second treatment with glucoamylase.

When a raw material to be used in the present invention is starch or the like, a part of which is modified with a phosphate group, a pre-treatment is required for detecting the glucoamylase-resistant component. For example, a reaction product is dissolved in a 10 mM carbonate buffer (pH 9.4, containing 10 mM $MgCl_2$ and 0.3 mM $ZnCl_2$), phosphatase is added to allow them to react, and thereafter, ethanol in a 10-fold amount is added, and a precipitate is collected. A glucoamylase-resistant component can be obtained by applying the aforementioned method to this precipitate.

The average degree of polymerization and constituent component of the glucoamylase-resistant component can be determined by analyzing a saccharide generated by reacting the glucoamylase-resistant component and glucan hydrolases, as described in the aforementioned (1) to (5). Examples of the hydrolysis include glucoamylase alone, a combination of glucoamylase and isoamylase, or a combination of glucoamylase and α-amylase. The reaction is performed, for example, by dissolving a glucoamylase-resistant component in distilled water to be 0.2% (w/v), adding each of the aforementioned hydrolases at an appropriate amount, and allowing to react them at 30 to 45° C. for an appropriate time (e.g., 1 hour). This degraded product of glucoamylase-resistant component is subjected to a saccharide analysis system manufactured by Dionex (liquid transfer system: DX300, detector: PAD-2, column: Carbo Pac PA100), and analyzed. The elution is performed, for example, under the conditions of a flow rate: 1 ml/minute, an NaOH concentration: 150 mM, a sodium acetate concentration: 0 minute-50 mM, 2 minutes-50 mM, 37 minutes-350 mM, 45 minutes-850 mM, and 47 minutes-850 mM. By this analysis, the average degree of polymerization of the glucoamylase-resistant component, and a saccharide generated by degradation can be determined.

5. Uses of Glucan Obtained by the Method of the Present Invention

The cyclic-structure-containing branched glucan obtained by the method of the present invention can be used for various utilities for starch. Particularly, it can be used in peritoneal dialysis, foods for diabetic patients, infusion solutions, compositions for beverage or food, compositions for food additives, and compositions for adhesion, and as an anti-retrogradation agent for starch. In these uses, the glucan of the present invention can be used at a concentration suitable for each use. Since the cyclic-structure-containing branched glucan of the present invention has a molecular weight in a range suitable for peritoneal dialysis, and contains little or no reducing saccharide, the cyclic-structure-containing branched glucan of the present invention is particularly suitable for peritoneal dialysis.

In the method of the present invention, little or no glucose and little or no low-molecular weight maltooligosaccharide are generated, and thus, a cyclic-structure-containing branched glucan not containing non-cyclic glucan byproducts (i.e., byproducts having a reducing end) such as glucose and maltooligosaccharide can be obtained without high level purification. Since the cyclic-structure-containing branched glucan not containing glucose and maltooligosaccharide is not rapidly absorbed into a body fluid, or does not rapidly elevate a blood sugar level, the glucan is particularly useful in peritoneal dialysis, and foods and infusion solutions for diabetic patient.

The cyclic-structure-containing branched glucan has excellent properties such that solubility in water is much higher, and viscosity of a starch paste in which the glucan is dissolved is lower, than the aforementioned raw material such as conventional starch, and retrogradation, which is observed in normal starch, does not occur. Further, since the cyclic-structure-containing branched glucan or a derivative thereof has low reactivity, it has an excellent property such that, when it is mixed with a protein or an amino acid and heated, it is difficult to be colored, as compared with conventional starch syrup and dextrin.

As described above, since the cyclic-structure-containing branched glucan has very high solubility in water, it can be suitably used for a powdering base material, coffee, soy sauce, tare sauce, sauce for noodles, sauce, dashi-no-moto (soup stock base), stew sauce mix, soup mix, composite seasoning, curry sauce mix, jelly, caramel, gum, chocolate, cookie, cracker, ice cream, sherbet, juice, powdered juice, bath additive, oral medicine, powdered drug, paint, adhesive, thickener, starch adhesive and the like.

Since the cyclic-structure-containing branched glucan does not undergo retrogradation, it can be suitably used in fresh Traditional Japanese-style confectioneries, fresh Western-style confectioneries, frozen food, refrigerated food, rice cake, rice ball and the like.

Since the cyclic-structure-containing branched glucan or a derivative thereof is such that the viscosity of a starch paste in which the glucan or derivative is dissolved is low, it can be suitably used in a raw material for biodegradable plastic, an intermediate substance for during production of cyclodextrin or the like from starch, a raw material in starch processing industry and the like.

The cyclic-structure-containing branched glucan has good adhesive property, and can be suitably used as a composition for adhesion.

Since the cyclic-structure-containing branched glucan has the same fundamental structure as that of normal starch except for a cyclic structure, it can be easily degraded to glucose by an enzyme in a living body, and thus, it is excellent in digestion property. For this reason, it can be also used in sports beverages, sports foods and the like.

The present invention will be described below by way of Examples, but the present invention is not limited to only these Examples.

EXAMPLES

Production Example 1

Production of Aquifex Aeolicus-Derived BE (AqBE)

From an *Escherichia coli* TG-1 strain possessing recombinant plasmid pAQBE1 described in Production Example 1 of Japanese Laid-Open Publication No. 2008-95117, an enzyme liquid containing AqBE having an amino acid sequence of SEQ ID NO: 2 was obtained by the method described in the same patent document.

Production Example 2

Production of *Rhodothemus Obamensis*-Derived BE (RhBE)

From an *Escherichia coli* TG-1 strain possessing recombinant plasmid pRBE1 described in Production Example 5 of Japanese Laid-Open Publication No. 2008-95117, an enzyme liquid containing RhBE having an amino acid sequence of SEQ ID NO: 4 was obtained by the method described in the same patent document.

Comparative Example 1

Trial to Produce Branched Glucan Having Cyclic Structure (1)

5 g of commercially available waxy corn starch was suspended in 100 ml of a 30 mM citrate buffer (pH 6.7), and this suspension was heated to 90° C. As a result, the starch was rapidly gelatinized, and this suspension changed to a hard rice cake state having no flowability. Although 0.15 ml (600 U/g substrate) of the AqBE enzyme liquid obtained in Production Example 1 was added to this gel-like suspension at 90° C. which has no flowability, a glucan having a cyclic structure was not produced.

Comparative Example 2

Trial of Production of Branched Glucan Having Cyclic Structure (2)

5 g of commercially available waxy corn starch was suspended in 100 ml of a 30 mM citrate buffer (pH 6.7), and this suspension was heated to 80° C. As a result, starch gelatinization occurred, and this suspension changed to a rice cake state having no flowability. Although 0.15 ml (600 U/g substrate) of the AqBE enzyme liquid obtained in Production Example 1 was added to this gel-like suspension at 80° C. which has no flowability, a glucan product having a cyclic structure was not produced.

Comparative Example 3

Production of Branched Glucan Having Cyclic Structure (3)

1 g of commercially available waxy corn starch was suspended in 100 ml of a 30 mM citrate buffer (pH 6.7), and to this suspension at 50° C. was added 0.15 ml (600 U/g substrate) of the AqBE enzyme liquid obtained in Production Example 1 to obtain a reaction mixed liquid, and this reaction mixed liquid was allowed to react at 70° C. for 16 hours with stirring. Then, the reaction mixed liquid was heated at 100° C. for 10 minutes. Then it was centrifuged at 6,500 rpm for 10 minutes to remove a precipitate, and the supernatant was filtered with a membrane having a pore diameter of 0.8 μm. A 2-fold amount of ethanol was added to the filtrate to allow precipitate to be generated. This precipitate was lyophilized to obtain about 0.28 g of a powdery glucan. As a result of examination of the glucan in the same manner as in Example 1, it was found that the weight-average molecular weight thereof was 138 kDa.

The determination of a structure of this glucan was performed in the same manner as in Example 1 described below, and it was confirmed that this glucan certainly had a cyclic structure and a branched structure, and the reducing ends thereof did not increase from those of the starch used as a starting substance.

However, in this production method, the yield of a branched glucan having a cyclic structure was about 28%, which was very low.

Comparative Example 4

Production of Branched Glucan Having Cyclic Structure (4)

5 g of commercially available waxy corn starch was added in 100 ml of a 30 mM citrate buffer (pH 6.7), and 0.15 ml (600 U/g substrate) of the AqBE enzyme liquid obtained in Production Example 1 was added to this suspension at 50° C. The suspension was allowed to react at 70° C. for 16 hours with stirring. The reaction mixed liquid was heated at 100° C. for 10 minutes. Then it was centrifuged at 6,500 rpm for 10 minutes to remove a precipitate, and then the supernatant was filtered with a membrane having a pore diameter of 0.8 μm. A 2-fold amount of ethanol was added to the filtrate to allow precipitate to be generated. This precipitate was lyophilized to obtain about 0.35 g of a powdery glucan. As a result of examination of the glucan in the same manner as in Example 1, it was found that the weight-average molecule weight thereof was 157 kDa.

The determination of a structure of this glucan was performed in the same manner as in Example 1 described below, and it was confirmed that this glucan certainly had a cyclic structure and a branched structure, and the number of reducing ends thereof did not increase as compared with those of the starch used as a starting substance.

However, in this production method, the yield of a branched glucan having a cyclic structure was about 35%, which was very low.

Comparative Example 5

Production of Branched Glucan Having Cyclic Structure (5)

50 g of commercially available waxy corn starch was suspended in 1 L of a 30 mM citrate buffer (pH 6.7), and 0.15 ml (6000 U/g substrate) of the AqBE enzyme liquid obtained in Production Example 1 was added to this suspension at 50° C. The suspension was allowed to react at 70° C. for 16 hours with stirring. The reaction mixed liquid was heated at 100° C. for 20 minutes. Then it was centrifuged at 6,500 rpm for 10 minutes to remove a precipitate, and the supernatant was filtered with a membrane having a pore diameter of 0.8 μm. A 2-fold amount of ethanol was added to the filtrate to allow precipitate to be generated. This precipitate was lyophilized to obtain about 1.1 g of a powdery glucan. As a result of examination of the glucan in the same manner as in Example 1, it was found that the weight-average molecular weight thereof was 119 kDa.

The determination of a structure of this glucan was performed in the same manner as in Example 1 described below, and it was confirmed that this glucan certainly had a cyclic structure and a branched structure, and reducing ends thereof did not increase from those of the starch used as a starting substance.

However, in this production method, the yield of a branched glucan having a cyclic structure was about 22%, which was very low.

Example 1

Production of Branched Glucan Having Cyclic Structure, Wherein the Reaction Temperature of Second Step was at 85° C.

50 g of commercially available waxy corn starch was suspended in 1 L of a 30 mM of citrate buffer (pH 6.7), and 0.15 ml (6000 U/g substrate) of the AqBE enzyme liquid obtained in Production Example 1 was added to this suspension at 50° C. The suspension was allowed to react at 70° C. for 6 hours with stirring, and then the temperature was raised to 85° C. and the suspension was allowed to react for 1 hour. At that time, the reaction mixed liquid had high transparency, and retained sufficient flowability. Further, the reaction mixed liquid was allowed to react at 70° C. for 16 hours. The reaction mixed liquid was heated at 100° C. for 20 minutes. Then it was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 44 g of a powdery glucan. That is, the yield of a branched glucan having a cyclic structure was about 88%. In this method, a quality problem for a final product such as burning or coloring of a powdery glucan did not occur.

The weight-average molecular weight of the glucan was examined using a high performance liquid chromatography (HPLC) system (column: OHPAK SB-806 MHQ, manufactured by SHOWA DENKO K.K.) equipped with a multi-angle laser-light scattering detector (DAWN DSP, manufactured by Wyatt Technology Corporation) and a differential refractometer (Shodex RI-71, manufactured by SHOWA DENKO K.K.). 20 mg of a powder of the branched glucan was dissolved in 10 ml of a 100 mM aqueous sodium nitrate solution, and the resultant mixture was filtered with a membrane having a pore diameter of 0.45 μm to obtain a filtrate. 100 μl of the resulting filtrate was injected into the aforementioned HPLC system, and measurement was performed. It was found that the weight-average molecular weight of this glucan was 111 kDa.

The determination of a structure of this glucan was performed according to the method described in Example 3 of Japanese Patent Gazette No. 3107358, and it was confirmed that this glucan certainly had a cyclic structure, and reducing ends thereof did not increase from those of the starch used as a starting substance. Further, by obtaining the number of non-reducing ends, it was also confirmed that this glucan had branching. The number of non-reducing ends of the glucan was obtained by examining the reducing power of the aforementioned glucan on which isoamylase was allowed to act, using the Modified Park-Johnson method (Hizukuri et al., Starch, Vol., 35, pp. 348-350 (1983)). Thus, the generated glucan was a cyclic-structure-containing branched glucan.

Example 2

Production of Branched Glucan Having Cyclic Structure Wherein the Reaction Temperature of Second Step was 100° C.

50 g of commercially available waxy corn starch was suspended in 1 L of a 30 mM of citrate buffer (pH 6.7), and 2.5 ml (1000 U/g substrate) of the AqBE enzyme liquid obtained in Production Example 1 was added to this suspension at 50° C. The suspension was allowed to react at 70° C. for 6 hours with stirring, and then the temperature was raised to 100° C., and was retained for 20 minutes. At that time, the reaction mixed liquid had high transparency, and retained sufficient flowability. 2.5 ml (1000 U/g substrate) of the AqBE enzyme liquid was added to the mixed liquid, and the mixed liquid was further allowed to react at 70° C. for 16 hours. The reaction mixed liquid was heated at 100° C. for 20 minutes. Then it was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 39 g of a powdery glucan. That is, the yield of a branched glucan having a cyclic structure was about 78%. As a result of examination of the glucan in the same manner as in Example 1, it was found that the weight-average molecular weight thereof was 164 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 3

Production of Branched Glucan Having Cyclic Structure Produced Using Starch Concentration of 10% (1))

100 g of commercially available waxy corn starch was suspended in 1 L of a 30 mM of citrate buffer (pH 6.7), and 5 ml (1000 U/g substrate) of the AqBE enzyme liquid obtained in Production Example 1 was added to this suspension at 50° C. The suspension was allowed to react at 70° C. for 16 hours with stirring, and then the temperature was raised to 100° C., and was retained for 20 minutes. At that time, the reaction mixed liquid had high transparency, and retained sufficient flowability. 5 ml (1000 U/g substrate) of the AqBE enzyme liquid was added to the mixed liquid, and the reaction mixed liquid was further allowed to react at 70° C. for 16 hours. The reaction mixed liquid was heated at 100° C. for 20 minutes. Then the reaction mixed liquid was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 76 g of a powdery glucan. That is, the yield of a branched glucan having a cyclic structure was about 76%. As a result of examination of the glucan in the same manner as in Example 1, it was found that the weight-average molecular weight thereof was 171 kDa. In this method, a quality problem for a final product such as burning or coloring of a powdery glucan did not occur.

The determination of a structure of this glucan was performed in the same manner as in Example 1, and it could be confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 4

Production of Branched Glucan Having Cyclic Structure Produced Using Starch Concentration of 10% (2)

2 g of commercially available waxy corn starch was suspended in 19.5 ml of a 30 mM of citrate buffer (pH 6.7), and 0.5 ml (5000 U/g substrate) of the AqBE enzyme liquid obtained in Production Example 1 was added to this suspension at 50° C. The suspension was allowed to react at 70° C. for 24 hours with stirring, and then the temperature was raised to 100° C., and retained for 20 minutes. At that time, the reaction mixed liquid had high transparency, and retained sufficient flowability. The reaction mixed liquid was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 1.6 g of a powdery glucan. That is, the yield of a branched glucan having a cyclic structure was about 80%. As a result of examination of the glucan in the same manner as in Example 1, it was found that the weight-average molecular weight thereof was 314 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 5

Production of Branched Glucan Having Cyclic Structure Produced Using Starch Concentration of 20%

4 g of commercially available waxy corn starch was suspended in 19 ml of a 30 mM of citrate buffer (pH 6.7), and 1 ml (5000 U/g substrate) of the AqBE enzyme liquid obtained in Production Example 1 was added to this suspension at 50° C. The suspension was allowed to react at 70° C. for 24 hours with stirring, and then the temperature was raised to 100° C., and retained for 20 minutes. At that time, the reaction mixed liquid had high transparency, and retained sufficient flowability. The reaction mixed liquid was centrifuged at 6,500 rpm for 10 minutes, and then the supernatant was filtered with a membrane having a pore diameter of 0.8 μm. A 2-fold amount of ethanol was added to the filtrate to allow precipitate to be generated. This precipitate was lyophilized to obtain about 3 g of a powdery glucan. That is, the yield of a branched glucan having a cyclic structure was about 75%. As a result of examination of the glucan in the same manner as in Example 1, it was found that the weight-average molecular weight thereof was 294 kDa. In this method, a quality problem for a final product such as burning or coloring of a powdery glucan was not caused.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 6

Production of Branched Glucan Having Cyclic Structure Produced Using Starch Concentration of 30%

6 g of commercially available waxy corn starch was suspended in 18.5 ml of a 30 mM of citrate buffer (pH 6.7), and 1.5 ml (5000 U/g substrate) of the AqBE enzyme liquid obtained in Production Example 1 was added to this suspension at 50° C. The suspension was allowed to react at 70° C. for 24 hours with stirring, and then the temperature was raised to 100° C., and retained for 20 minutes. At that time, the reaction mixed liquid had high transparency, and retained sufficient flowability. The reaction mixed liquid was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 5 g of a powdery glucan. That is, the yield of a branched glucan having a cyclic structure was about 83%. As a result of examination of the glucan in the same manner as in Example 1, it was found that the weight-average molecular weight thereof was 324 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 7

Production of Branched Glucan Having Cyclic Structure Wherein the Reaction Temperature of First Step was at 65° C.

100 g of commercially available waxy corn starch was suspended in 1 L of a 30 mM of citrate buffer (pH 6.7), and 5 ml (5000 U/g substrate) of the AqBE enzyme liquid obtained in Production Example 1 was added to this suspension at 50° C. The suspension was allowed to react at 65° C. for 6 hours with stirring, and then the temperature was raised to 100° C., and retained for 20 minutes. At that time, the reaction mixed liquid had high transparency, and retained sufficient flowability. 5 ml (5000 U/g substrate) of the AqBE enzyme liquid was further added to the mixed liquid, and the mixed liquid was further allowed to react at 65° C. for 16 hours. The reaction mixed liquid was heated at 100° C. for 20 minutes. Then the reaction mixed liquid was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 81 g of a powdery glucan. That is, the yield of a branched glucan having a cyclic structure was about 81%. As a result of examination of the glucan in the same manner as in Example 1, it was found that the weight-average molecular weight thereof was 141 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 8

Production of Branched Glucan Having Cyclic Structure Using *Rhodothermus Obamensis*-Derived BE (RhBE)

50 g of commercially available waxy corn starch was suspended in 1 L of a 30 mM of citrate buffer (pH 6.7), and 2.5 ml (5000 U/g substrate) of the RhBE enzyme liquid obtained in Production Example 2 was added to this suspension at 50° C. The suspension was allowed to react at 65° C. for 6 hours with stirring, the temperature was raised to 100° C., and retained for 20 minutes. At that time, the reaction mixed liquid had high transparency, and retained sufficient flowability. 2.5 ml (5000 U/g substrate) of the RBE enzyme liquid was added to the mixed liquid, and the reaction mixed liquid was further allowed to react at 65° C. for 16 hours. The reaction mixed liquid was heated at 100° C. for 20 minutes. Then the reaction mixed liquid was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 41 g of a powdery glucan. That is, the yield of a branched glucan having a cyclic structure was about 82%. As a result of examination of the glucan in the same manner as in Example 1, it was found that the weight-average molecular weight thereof was 140 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 9

Production of Cyclic Glucan by be Instantaneous Continuous Reaction Method (95° C.)

50 g of commercially available waxy corn starch was suspended in 1 L of a 30 mM of citrate buffer (pH 6.7), and 50 mL (50,000 U/g substrate) of the AqBE enzyme liquid obtained in Production Example 1 was added to this suspension at 50° C. The temperature was rapidly raised to 95° C. with stirring the suspension, and was retained at 95° C. for 5 minutes to liquefy the waxy corn starch, and then the temperature was lowered to 70° C., 1 mL (1000 U/g substrate) of the AqBE enzyme liquid was further added, and the mixture was allowed to react for 16 hours. The reaction solution was heated at 100° C. for 20 minutes. Then the reaction solution was centrifuged at 6,500 rpm for 10 minutes, and then the supernatant was filtered with a membrane having a pore diameter of 0.8 μm. A 2-fold amount of ethanol was added to the filtrate to allow precipitate to be generated. This precipitate was lyophilized to obtain about 39 g of a powdery glucan. That is, the yield of a branched glucan having a cyclic structure was about 78%. As a result of examination of the glucan in the same manner as in Example 1, it was found that the weight-average molecular weight thereof was 139 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 10

Production of Cyclic Glucan by BE Instantaneous Continuous Reaction Method (100° C.))

50 g of commercially available waxy corn starch was suspended in 1 L of a 30 mM of citrate buffer (pH 6.7), and 50,000 U/g substrate of RhBE obtained in Production Example 2 was added to this suspension at 50° C. The temperature was rapidly raised to 100° C. with stirring the suspension, and then was retained at 100° C. for 5 minutes to liquefy the waxy corn starch, and then the temperature was lowered to 70° C., 1000 U/g substrate of the RhBE was added, and the mixture was allowed to react for 16 hours. The reaction solution was heated at 100° C. for 20 minutes. Then the reaction solution was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 37 g of a powdery glucan. That is, the yield of a branched glucan having a cyclic structure was about 74%. As a result of examination of the glucan in the same manner as in Example 1, it was found that the weight-average molecular weight thereof was 141 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 11

Production of Branched Glucan Having Cyclic Structure Produced Using Normal Corn Starch Concentration of 10%

100 g of commercially available normal corn starch was suspended in 1 L of a 30 mM of citrate buffer (pH 6.7), and 5 ml (1000 U/g substrate) of the AqBE enzyme liquid obtained in Production Example 1 was added to this suspension at 50° C. The suspension was allowed to react at 70° C. for 2 hours with stirring, and then the temperature was raised to 120° C., and was retained for 60 minutes. At that time, the reaction mixed liquid had high transparency, and retained sufficient flowability. 5 ml (1000 U/g substrate) of the AqBE enzyme liquid was added to the reaction mixed liquid, and the reaction mixed liquid was further allowed to react at 70° C. for 16 hours. The reaction mixed liquid was heated at 100° C. for 20 minutes. Then the reaction mixed liquid was centrifuged at 6,500 rpm for 10 minutes, and the supernatant was filtered with a membrane having a pore diameter of 0.8 μm. A 2-fold amount of ethanol was added to the filtrate to allow precipitate to be generated. This precipitate was lyophilized to obtain about 79 g of a powdery glucan. That is, the yield of a branched glucan having a cyclic structure was about 79%. As a result of examination of the glucan in the same manner as in Example 1, it was found that the weight-average molecular weight thereof was 188 kDa. In this method, a quality problem for a final product such as burning or coloring of a powdery glucan did not occur.

The determination of a structure of this glucan was performed in the same manner as in Example 1, and it could be confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 12

Production of Branched Glucan Having Cyclic Structure Produced Using Potato Starch Concentration of 10%

100 g of commercially available potato starch was suspended in 1 L of a 30 mM of citrate buffer (pH 6.7), and 5 ml (1000 U/g substrate) of the AqBE enzyme liquid obtained in Production Example 1 was added to this suspension at 50° C. The suspension was allowed to react at 70° C. for 2 hours with stirring, and then the temperature was raised to 120° C., and was retained for 60 minutes. At that time, the reaction mixed liquid had high transparency, and retained sufficient flowability. 6 ml (1200 U/g substrate) of the AqBE enzyme liquid was added to the reaction mixed liquid, and the reaction mixed liquid was further allowed to react at 70° C. for 16 hours. The reaction mixed liquid was heated at 100° C. for 20 minutes. Then the reaction mixed liquid was centrifuged at 6,500 rpm for 10 minutes, and then the supernatant was filtered with a membrane having a pore diameter of 0.8 μm. A 2-fold amount of ethanol was added to the filtrate to allow precipitate to be generated. This precipitate was lyophilized to obtain about 81 g of a powdery glucan. That is, the yield of a branched glucan having a cyclic structure was about 81%. As a result of examination of the glucan in the same manner as in Example 1, it was found that the weight-average molecular weight thereof was 206 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

Example 13

Production of Branched Glucan Having Cyclic Structure Produced Using Tapioca Starch Concentration of 10%

100 g of commercially available tapioca starch was suspended in 1 L of a 30 mM of citrate buffer (pH 6.7), and 5 ml (1000 U/g substrate) of the AqBE enzyme liquid obtained in Production Example 1 was added to this suspension at 50° C. The suspension was allowed to react at 70° C. for 2 hours while stirring, and then the temperature was raised to 120° C., and was retained for 60 minutes. At that time, the reaction mixed liquid had high transparency, and retained sufficient flowability. 6 ml (1200 U/g substrate) of the AqBE enzyme liquid was added to the reaction mixed liquid, and the reaction mixed liquid was further allowed to react at 70° C. for 16 hours. The reaction mixed liquid was heated at 100° C. for 20 minutes. Then the reaction mixed liquid was centrifuged at 6,500 rpm for 10 minutes, and then the supernatant was filtered with a membrane having a pore diameter of 0.8 μm. A 2-fold amount of ethanol was added to the filtrate to allow precipitate to be generated. This precipitate was lyophilized to obtain about 82 g of a powdery glucan. That is, the yield of a branched glucan having a cyclic structure was about 82%. As a result of examination of the glucan in the same manner as in Example 1, it was found that the weight-average molecular weight thereof was 136 kDa. In this method, a quality problem for a final product such as burning or coloring of a powdery glucan did not occur.

The determination of a structure of this glucan was performed in the same manner as in Example 1, and it was confirmed that this glucan had certainly a cyclic structure, and the reducing ends thereof did not increase from those of the starch used as a starting substance. Further, by obtaining the number of non-reducing ends in the same manner as in Example 1, it was also confirmed that this glucan had branching. Thus, the generated glucan was a cyclic-structure-containing branched glucan.

The results of Comparative Examples 1 to 5 and Examples 1 to 13 are shown in Table 1 described below. It should be noted that when flowability is NO it corresponds to the case where a solution is placed into a plastic tube having a capacity of 1.5 ml immediately after enzyme treatment, and then the tube is immediately inverted, and maintained at the temperature of the final enzyme reaction for 10 minutes while the tube is open at the section beneath the solution, and 20% by weight or more of the placed solution remains in the tube, and when flowability is YES it corresponds to the case where a solution in an amount smaller than this amount remains in the tube. In the evaluation, when the flowability is NO or the yield of a product is less than 40%, the result is evaluated as NG (improper), in the other cases, the result is evaluated as YES (proper).

TABLE 1

|  | Starch granule concentration (% by weight) | BE amount (U/g substrate) | Temperature at enzyme addition | Reaction temperature | Raised temperature | Re-reaction temperature | Yield of product (%) | Molecular weight of product (×10³) | Flowability | Determination |
|---|---|---|---|---|---|---|---|---|---|---|
| Com. 1 | 5 | 600 | 90 | 90 | — | — | nt | nt | NO | NG |
| Com. 2 | 5 | 600 | 80 | 85 | — | — | nt | nt | NO | NG |
| Com. 3 | 1 | 600 | 50 | 70 | — | — | 28 | 138 | YES | NG |
| Com. 4 | 5 | 600 | 50 | 70 | — | — | 35 | 157 | YES | NG |
| Com. 5 | 5 | 6000 | 50 | 70 | — | — | 22 | 119 | YES | NG |
| Ex. 1 | 5 | 6000 | 50 | 70 | 85 | 70 | 88 | 111 | YES | YES |
| Ex. 2 | 5 | 1000 + 1000 | 50 | 70 | 100 | 70 | 78 | 164 | YES | YES |
| Ex. 3 | 10 | 1000 + 1000 | 50 | 70 | 100 | 70 | 76 | 171 | YES | YES |
| Ex. 4 | 10 | 5000 | 50 | 70 | 100 | — | 80 | 314 | YES | YES |
| Ex. 5 | 20 | 5000 | 50 | 70 | 100 | — | 75 | 294 | YES | YES |
| Ex. 6 | 30 | 5000 | 50 | 70 | 100 | — | 83 | 324 | YES | YES |
| Ex. 7 | 10 | 5000 + 5000 | 50 | 65 | 100 | 65 | 81 | 141 | YES | YES |
| Ex. 8 | 5 | 5000 + 5000 | 50 | 65 | 100 | 65 | 82 | 140 | YES | YES |
| Ex. 9 | 5 | 50000 + 1000 | 50 | — | 95 | 70 | 78 | 139 | YES | YES |
| Ex. 10 | 10 | 50000 + 1000 | 50 | — | 100 | 70 | 74 | 141 | YES | YES |

TABLE 1-continued

|  | Starch granule concentration (% by weight) | BE amount (U/g substrate) | Temperature at enzyme addition | Reaction temperature | Raised temperature | Re-reaction temperature | Yield of product (%) | Molecular weight of product (×10³) | Flowability | Determination |
|---|---|---|---|---|---|---|---|---|---|---|
| Ex. 11 | 10 | 1000 + 1000 | 50 | 70 | 120 | 70 | 79 | 188 | YES | YES |
| Ex. 12 | 10 | 1000 + 1200 | 50 | 70 | 120 | 70 | 81 | 206 | YES | YES |
| Ex. 13 | 10 | 1000 + 1200 | 50 | 70 | 120 | 70 | 82 | 136 | YES | YES |

Com.: Comparative Example,
Ex.: Example
Flowability NO = No flowability;
flowability YES = presence of flowability
Determination NG = improper;
determination YES = suitable As described above, the present invention has been exemplified using preferable embodiments of the present invention, but the present invention should not be construed so as to be limited to these embodiments. It is understood that the scope of the present invention should be construed only by claims. It is understood that those skilled in the art can carry out an equivalent scope based on the description of the present invention and common technical knowledge, from the description of specific preferable embodiments of the present invention. It is understood that the content of patents, patent applications and references cited in the present specification should be incorporated herein by reference, as if the content itself is specifically described in the present specification.

INDUSTRIAL APPLICABILITY

According to the method of the present invention, it is possible to produce a cyclic-structure-containing glucan having no reducing power at a high yield, and it is advantageous in respect of the efficiency of industrial production process.

Further, a cyclic-structure-containing branched glucan produced by the method of the present invention is useful in peritoneal dialysis, foods for diabetic patients, infusion solutions, compositions for beverage or food, compositions for food additives, and compositions for adhesion, and as an anti-retrogradation agent for starch. For example, when the branched glucan includes no reducing saccharide such as glucose and maltooligosaccharide, it is not rapidly absorbed in a body fluid, or dose not elevate a blood sugar level rapidly, and thus, it is particularly useful in peritoneal dialysis, foods for diabetic patient and infusion solutions.

Sequence Listing Free Text

SEQ ID NO: 1: Base sequence encoding the wild type BE of the *Aquifex aeolicus* VF5;

SEQ ID NO: 2: Amino acid sequence of the wild type BE of the *Aquifex aeolicus* VF5;

SEQ ID NO: 3: Base sequence encoding the wild type BE of the *Rhodothermus obamensis* JCM9785; and SEQ ID NO: 4: Amino acid sequence of the wild type BE of the *Rhodothermus obamensis* JCM9785.

The invention claimed is:

1. A method for producing a branched glucan having a cyclic structure comprising the steps of:
   (1) adding a branching enzyme before or during the gelatinization of starch granules, wherein the starch granules are suspended at a concentration of 5% by weight or more and 50% by weight or less in a mixed liquid, and allowing the branching enzyme to act on starch in the starch granules, wherein a temperature of the mixed liquid at the time of addition is 0° C. or higher and not higher than the gelatinization starting temperature of the starch granules; and
   (2) elevating the temperature of the mixed liquid to 85° C. or higher and 129° C. or lower, wherein in the method, none of α-amylase, β-amylase, amyloglucosidase and/or α-transglucosidase is added to the mixed liquid.

2. The method according to claim 1, wherein the temperature of the mixed liquid at the time of addition in step (1) is 0 to 67.5° C., and the method further includes, thereafter and before step (2), a step of raising the temperature of the mixed liquid to a temperature which is higher than the temperature of the mixed liquid at the time of addition and is within a range of 30 to 75° C. to thereby allow the branching enzyme to act on the starch in the starch granules.

3. The method according to claim 1, wherein the temperature of the mixed liquid at the time of addition in step (1) is 15 to 67.5° C., and the method further includes, thereafter and before step (2), a step of raising the temperature of the mixed liquid to a temperature which is higher than the temperature of the mixed liquid at the time of addition and is within a range of 30 to 75° C. to thereby allow the branching enzyme to act on the starch in the starch granules.

4. The method according to claim 1, wherein the temperature of the mixed liquid at the time of addition in step (1) is 20 to 50° C., and the method further includes, thereafter and before step (2), a step of raising the temperature of the mixed liquid to a temperature which is higher than the temperature of the mixed liquid at the time of addition and is within a range of 40 to 75° C. to thereby allow the branching enzyme to act on the starch in the starch granules.

5. The method according to claim 1, wherein the temperature of the mixed liquid at the time of addition in step (1) is 20 to 40° C., and the method further includes, thereafter and before step (2), a step of raising the temperature of the mixed liquid to a temperature which is higher than the temperature of the mixed liquid at the time of addition and is within a range of 50 to 75° C. to thereby allow the branching enzyme to act on the starch in the starch granules.

6. The method according to claim 1, wherein after the branching enzyme is added in step (1) the temperature elevation of step (2) is completed within a period of time of 10 seconds or longer and 72 hours or shorter, and the method further includes, after step (2), a step of lowering the temperature of the mixed liquid to 0° C. to 100° C. and then adding a branching enzyme to allow to act at 0° C. to 100° C.

7. The method according to claim 1, wherein after the branching enzyme is added in step (1) the temperature elevation of step (2) is completed within a period of time of 1 second or longer and 20 seconds or shorter, and the method further includes, after step (2), a step of lowering the temperature of the mixed liquid to 0° C. to 100° C. and then adding a branching enzyme to allow to act at 0° C. to 100° C.

8. The method according to claim 1, wherein after the branching enzyme is added in step (1) the temperature elevation of step (2) is completed within a period of time of 1 second or longer and 20 seconds or shorter, and the method further includes, after step (2), a step of lowering the temperature of the mixed liquid to 0° C. to 100° C. and then adding a branching enzyme to allow to act at 50° C. to 100° C.

9. The method according to claim 1, further comprising a step of removing insolubles from the mixed liquid after step (2).

10. The method of claim 1, wherein the branching enzyme has an activity in step (2).

11. The method according to claim 1, wherein the branching enzyme is an Aquifex aeolicus-derived branching enzyme or a Rhodothermus obamensis-derived branching enzyme.

* * * * *

UNITED STATES PATENT AND TRADEMARK OFFICE
CERTIFICATE OF CORRECTION

PATENT NO.        : 9,562,247 B2
APPLICATION NO.   : 13/992205
DATED             : February 7, 2017
INVENTOR(S)       : Takeshi Takaha et al.

Page 1 of 1

It is certified that error appears in the above-identified patent and that said Letters Patent is hereby corrected as shown below:

On the Title Page

Item (75):
"Takeshi Takaha, Osaka (JP); Kouji Odan, Osaka (JP); Michiyo Yanase, Osaka (JP); Iwao Kojima, Osaka (JP); Tsunehisa Akiyama, Osaka (JP)"
Should read:
--Takeshi Takaha, Osaka-shi (JP); Kouji Odan, Osaka-shi (JP); Michiyo Yanase, Osaka-shi (JP); Iwao Kojima, Osaka-shi (JP); Tsunehisa Akiyama, Osaka-shi (JP)--.

Item (56):
"Japanease Patent Gazette No. 3107358"
Should read:
--Japanese Patent Gazette No. 3107358--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

```
                        SEQUENCE LISTING

<160> NUMBER OF SEQ ID NOS: 4

<210> SEQ ID NO 1
<211> LENGTH: 1893
<212> TYPE: DNA
<213> ORGANISM: Aquifex aeolicus
<220> FEATURE:
<221> NAME/KEY: CDS
<222> LOCATION: (1)..(1893)

<400> SEQUENCE: 1 atg aag aag ttc agt ctc atc agt gat tac gac gtt tac ctc ttt aag      48
Met Lys Lys Phe Ser Leu Ile Ser Asp Tyr Asp Val Tyr Leu Phe Lys
1               5                   10                  15 gag gga acg cac acg aga ctt tac gat aaa ctt ggc tcc cac gtt ata      96
Glu Gly Thr His Thr Arg Leu Tyr Asp Lys Leu Gly Ser His Val Ile
            20                  25                  30 gaa cta aac ggg aaa agg tat acc ttc ttt gcg gtt tgg gca ccc cac     144
Glu Leu Asn Gly Lys Arg Tyr Thr Phe Phe Ala Val Trp Ala Pro His
        35                  40                  45 gcg gat tac gta tca ctt ata ggc gat ttt aac gaa tgg gat aaa ggt     192
Ala Asp Tyr Val Ser Leu Ile Gly Asp Phe Asn Glu Trp Asp Lys Gly
    50                  55                  60
```

-continued

```
tct act ccc atg gta aag agg gag gac ggc tcc gga ata tgg gag gtt     240
Ser Thr Pro Met Val Lys Arg Glu Asp Gly Ser Gly Ile Trp Glu Val
 65              70                  75                  80 tta ctt gaa gga gac ctg act ggt tca aag tac aag tac ttt ata aag     288
Leu Leu Glu Gly Asp Leu Thr Gly Ser Lys Tyr Lys Tyr Phe Ile Lys
                 85                  90                  95 aac ggg aat tac gaa gtt gat aag tcc gat ccc ttc gca ttt ttc tgt     336
Asn Gly Asn Tyr Glu Val Asp Lys Ser Asp Pro Phe Ala Phe Phe Cys
            100                 105                 110 gag caa ccc ccc gga aac gct tcc gta gtg tgg aag ctc aat tac agg     384
Glu Gln Pro Pro Gly Asn Ala Ser Val Val Trp Lys Leu Asn Tyr Arg
        115                 120                 125 tgg aac gac tcc gaa tac atg aaa aag agg aaa aga gta aac tca cac     432
Trp Asn Asp Ser Glu Tyr Met Lys Lys Arg Lys Arg Val Asn Ser His
    130                 135                 140 gac tcg cct ata tcc ata tac gaa gtt cac gtg ggt tct tgg agg aga     480
Asp Ser Pro Ile Ser Ile Tyr Glu Val His Val Gly Ser Trp Arg Arg
145                 150                 155                 160 gtt cca gaa gag gga aac aga ttt ttg agc tat agg gaa ctt gcc gaa     528
Val Pro Glu Glu Gly Asn Arg Phe Leu Ser Tyr Arg Glu Leu Ala Glu
                165                 170                 175 tac ctc cca tac tac gta aaa gag atg gga ttt act cac gtt gag ttc     576
Tyr Leu Pro Tyr Tyr Val Lys Glu Met Gly Phe Thr His Val Glu Phe
            180                 185                 190 tta ccc gtt atg gaa cat ccc ttt tac ggc tct tgg ggc tac cag ata     624
Leu Pro Val Met Glu His Pro Phe Tyr Gly Ser Trp Gly Tyr Gln Ile
        195                 200                 205 acg ggc tac ttc gct ccg act tcc aga tac gga act cct cag gac ttt     672
Thr Gly Tyr Phe Ala Pro Thr Ser Arg Tyr Gly Thr Pro Gln Asp Phe
    210                 215                 220 atg tac tta ata gac aaa ctt cat caa gaa ggg ata ggt gtg ata cta     720
Met Tyr Leu Ile Asp Lys Leu His Gln Glu Gly Ile Gly Val Ile Leu
225                 230                 235                 240 gac tgg gtt ccc tct cac ttt ccc acc gat gcc cac ggg ctc gca tac     768
Asp Trp Val Pro Ser His Phe Pro Thr Asp Ala His Gly Leu Ala Tyr
                245                 250                 255 ttt gac ggg act cac ctt tac gag tac gag gac tgg aga aag agg tgg     816
Phe Asp Gly Thr His Leu Tyr Glu Tyr Glu Asp Trp Arg Lys Arg Trp
            260                 265                 270 cat ccc gac tgg aac agc ttt gtt ttt gat tac gga aaa ccg gaa gtt     864
His Pro Asp Trp Asn Ser Phe Val Phe Asp Tyr Gly Lys Pro Glu Val
        275                 280                 285 cgc tcc ttt ctc ctg agt tct gcc cac ttc tgg ctc gac aag tac cac     912
Arg Ser Phe Leu Leu Ser Ser Ala His Phe Trp Leu Asp Lys Tyr His
    290                 295                 300 gca gac ggt ctc aga gtg gat gca gtt gct tca atg ctt tac cta gat     960
Ala Asp Gly Leu Arg Val Asp Ala Val Ala Ser Met Leu Tyr Leu Asp
305                 310                 315                 320 tac tct agg aaa gaa tgg gtt cca aac ata tac gga ggg aaa gaa aac    1008
Tyr Ser Arg Lys Glu Trp Val Pro Asn Ile Tyr Gly Gly Lys Glu Asn
                325                 330                 335 ctc gag gct ata gaa ttc ctc agg aag ttt aac gaa agc gtt tac aga    1056
Leu Glu Ala Ile Glu Phe Leu Arg Lys Phe Asn Glu Ser Val Tyr Arg
            340                 345                 350 aat ttt cca gac gtc cag aca ata gcg gag gaa tca aca gcc tgg cct    1104
Asn Phe Pro Asp Val Gln Thr Ile Ala Glu Glu Ser Thr Ala Trp Pro
        355                 360                 365 atg gtg tcc aga cct aca tac gtg ggg gga ctg gga ttt gga atg aag    1152
Met Val Ser Arg Pro Thr Tyr Val Gly Gly Leu Gly Phe Gly Met Lys
```

-continued

```
                  370                 375                 380
tgg aat atg ggt tgg atg aac gac aca ctc ttt tac ttt tca aag gat   1200
Trp Asn Met Gly Trp Met Asn Asp Thr Leu Phe Tyr Phe Ser Lys Asp
385                 390                 395                 400 ccc atc tac agg aag tac cac cat gaa gtc ctc act ttc agt ata tgg   1248
Pro Ile Tyr Arg Lys Tyr His His Glu Val Leu Thr Phe Ser Ile Trp
                405                 410                 415 tac gct ttt tcc gag aac ttc gtc ctt cca cta tcc cac gat gaa gtt   1296
Tyr Ala Phe Ser Glu Asn Phe Val Leu Pro Leu Ser His Asp Glu Val
            420                 425                 430 gtt cac gga aag ggt tct ctg ata ggg aag atg cca gga gat tac tgg   1344
Val His Gly Lys Gly Ser Leu Ile Gly Lys Met Pro Gly Asp Tyr Trp
        435                 440                 445 cag aag ttt gca aac ctt aga gcc ctt ttc gga tac atg tgg gca cac   1392
Gln Lys Phe Ala Asn Leu Arg Ala Leu Phe Gly Tyr Met Trp Ala His
    450                 455                 460 cca ggg aaa aaa ctc ctc ttt atg ggg gga gag ttc gga cag ttt aag   1440
Pro Gly Lys Lys Leu Leu Phe Met Gly Gly Glu Phe Gly Gln Phe Lys
465                 470                 475                 480 gaa tgg gat cac gaa acg agt ctc gac tgg cac ctc ttg gaa tac cct   1488
Glu Trp Asp His Glu Thr Ser Leu Asp Trp His Leu Leu Glu Tyr Pro
                485                 490                 495 tct cac aga ggt att cag aga tta gtt aag gac tta aac gaa gtt tac   1536
Ser His Arg Gly Ile Gln Arg Leu Val Lys Asp Leu Asn Glu Val Tyr
            500                 505                 510 agg agg gaa aag gct ttg cac gaa acg gat ttt tca cct gag ggc ttt   1584
Arg Arg Glu Lys Ala Leu His Glu Thr Asp Phe Ser Pro Glu Gly Phe
        515                 520                 525 gag tgg gta gac ttc cac gac tgg gaa aag agc gtt ata tcc ttc ttg   1632
Glu Trp Val Asp Phe His Asp Trp Glu Lys Ser Val Ile Ser Phe Leu
    530                 535                 540 aga aag gac aaa agc ggt aag gaa att ata ctc gta gtt tgc aac ttc   1680
Arg Lys Asp Lys Ser Gly Lys Glu Ile Ile Leu Val Val Cys Asn Phe
545                 550                 555                 560 aca ccc gtt ccg aga tac gat tac agg gta ggt gta ccg aaa ggc gga   1728
Thr Pro Val Pro Arg Tyr Asp Tyr Arg Val Gly Val Pro Lys Gly Gly
                565                 570                 575 tac tgg agg gag ata atg aat acc gat gca aag gag tac tgg ggc tcc   1776
Tyr Trp Arg Glu Ile Met Asn Thr Asp Ala Lys Glu Tyr Trp Gly Ser
            580                 585                 590 gga atg gga aat ctg ggt gga aaa gag gct gat aaa atc ccg tgg cac   1824
Gly Met Gly Asn Leu Gly Gly Lys Glu Ala Asp Lys Ile Pro Trp His
        595                 600                 605 gga aga aaa ttc tca ctt tca ctt acc ctg cct ccc ctt tcc gtg atc   1872
Gly Arg Lys Phe Ser Leu Ser Leu Thr Leu Pro Pro Leu Ser Val Ile
    610                 615                 620 tat tta aag cac gaa gga tga                                       1893
Tyr Leu Lys His Glu Gly
625                 630

<210> SEQ ID NO 2
<211> LENGTH: 630
<212> TYPE: PRT
<213> ORGANISM: Aquifex aeolicus

<400> SEQUENCE: 2

Met Lys Lys Phe Ser Leu Ile Ser Asp Tyr Asp Val Tyr Leu Phe Lys
1               5                   10                  15

Glu Gly Thr His Thr Arg Leu Tyr Asp Lys Leu Gly Ser His Val Ile
            20                  25                  30
```

Glu Leu Asn Gly Lys Arg Tyr Thr Phe Phe Ala Val Trp Ala Pro His
            35                  40                  45

Ala Asp Tyr Val Ser Leu Ile Gly Asp Phe Asn Glu Trp Asp Lys Gly
        50                  55                  60

Ser Thr Pro Met Val Lys Arg Glu Asp Gly Ser Gly Ile Trp Glu Val
65                  70                  75                  80

Leu Leu Glu Gly Asp Leu Thr Gly Ser Lys Tyr Lys Tyr Phe Ile Lys
                85                  90                  95

Asn Gly Asn Tyr Glu Val Asp Lys Ser Asp Pro Phe Ala Phe Phe Cys
                100                 105                 110

Glu Gln Pro Pro Gly Asn Ala Ser Val Val Trp Lys Leu Asn Tyr Arg
            115                 120                 125

Trp Asn Asp Ser Glu Tyr Met Lys Lys Arg Lys Arg Val Asn Ser His
            130                 135                 140

Asp Ser Pro Ile Ser Ile Tyr Glu Val His Val Gly Ser Trp Arg Arg
145                 150                 155                 160

Val Pro Glu Glu Gly Asn Arg Phe Leu Ser Tyr Arg Glu Leu Ala Glu
                165                 170                 175

Tyr Leu Pro Tyr Tyr Val Lys Glu Met Gly Phe Thr His Val Glu Phe
                180                 185                 190

Leu Pro Val Met Glu His Pro Phe Tyr Gly Ser Trp Gly Tyr Gln Ile
            195                 200                 205

Thr Gly Tyr Phe Ala Pro Thr Ser Arg Tyr Gly Thr Pro Gln Asp Phe
            210                 215                 220

Met Tyr Leu Ile Asp Lys Leu His Gln Glu Gly Ile Gly Val Ile Leu
225                 230                 235                 240

Asp Trp Val Pro Ser His Phe Pro Thr Asp Ala His Gly Leu Ala Tyr
                245                 250                 255

Phe Asp Gly Thr His Leu Tyr Glu Tyr Glu Asp Trp Arg Lys Arg Trp
                260                 265                 270

His Pro Asp Trp Asn Ser Phe Val Phe Asp Tyr Gly Lys Pro Glu Val
            275                 280                 285

Arg Ser Phe Leu Leu Ser Ser Ala His Phe Trp Leu Asp Lys Tyr His
            290                 295                 300

Ala Asp Gly Leu Arg Val Asp Ala Val Ala Ser Met Leu Tyr Leu Asp
305                 310                 315                 320

Tyr Ser Arg Lys Glu Trp Val Pro Asn Ile Tyr Gly Gly Lys Glu Asn
                325                 330                 335

Leu Glu Ala Ile Glu Phe Leu Arg Lys Phe Asn Glu Ser Val Tyr Arg
                340                 345                 350

Asn Phe Pro Asp Val Gln Thr Ile Ala Glu Glu Ser Thr Ala Trp Pro
            355                 360                 365

Met Val Ser Arg Pro Thr Tyr Val Gly Gly Leu Gly Phe Gly Met Lys
            370                 375                 380

Trp Asn Met Gly Trp Met Asn Asp Thr Leu Phe Tyr Phe Ser Lys Asp
385                 390                 395                 400

Pro Ile Tyr Arg Lys Tyr His His Glu Val Leu Thr Phe Ser Ile Trp
                405                 410                 415

Tyr Ala Phe Ser Glu Asn Phe Val Leu Pro Leu Ser His Asp Glu Val
                420                 425                 430

Val His Gly Lys Gly Ser Leu Ile Gly Lys Met Pro Gly Asp Tyr Trp
            435                 440                 445

```
Gln Lys Phe Ala Asn Leu Arg Ala Leu Phe Gly Tyr Met Trp Ala His
    450                 455                 460

Pro Gly Lys Lys Leu Leu Phe Met Gly Gly Glu Phe Gly Gln Phe Lys
465                 470                 475                 480

Glu Trp Asp His Glu Thr Ser Leu Asp Trp His Leu Leu Glu Tyr Pro
                485                 490                 495

Ser His Arg Gly Ile Gln Arg Leu Val Lys Asp Leu Asn Glu Val Tyr
                500                 505                 510

Arg Arg Glu Lys Ala Leu His Glu Thr Asp Phe Ser Pro Glu Gly Phe
                515                 520                 525

Glu Trp Val Asp Phe His Asp Trp Glu Lys Ser Val Ile Ser Phe Leu
530                 535                 540

Arg Lys Asp Lys Ser Gly Lys Glu Ile Ile Leu Val Val Cys Asn Phe
545                 550                 555                 560

Thr Pro Val Pro Arg Tyr Asp Tyr Arg Val Gly Val Pro Lys Gly Gly
                565                 570                 575

Tyr Trp Arg Glu Ile Met Asn Thr Asp Ala Lys Glu Tyr Trp Gly Ser
                580                 585                 590

Gly Met Gly Asn Leu Gly Gly Lys Glu Ala Asp Lys Ile Pro Trp His
                595                 600                 605

Gly Arg Lys Phe Ser Leu Ser Leu Thr Leu Pro Pro Leu Ser Val Ile
610                 615                 620

Tyr Leu Lys His Glu Gly
625                 630

<210> SEQ ID NO 3
<211> LENGTH: 1866
<212> TYPE: DNA
<213> ORGANISM: Rhodothermus obamensis
<220> FEATURE:
<221> NAME/KEY: CDS
<222> LOCATION: (1)..(1866)

<400> SEQUENCE: 3 atg agc tgg ctc acg gaa gaa gac atc cgg cgc tgg gaa agc ggt acg      48
Met Ser Trp Leu Thr Glu Glu Asp Ile Arg Arg Trp Glu Ser Gly Thr
1               5                   10                  15 ttc tac gac agt tac cga aag ctg ggc gcc cat ccc gac gac gaa ggc      96
Phe Tyr Asp Ser Tyr Arg Lys Leu Gly Ala His Pro Asp Asp Glu Gly
                20                  25                  30 acc tgg ttc tgc gtc tgg gcg ccg cat gcc gat ggc gtc tcg gtg ctc     144
Thr Trp Phe Cys Val Trp Ala Pro His Ala Asp Gly Val Ser Val Leu
            35                  40                  45 gga gcg ttc aac gac tgg aat ccg gag gcc aac ccg ctg gag cgc tac     192
Gly Ala Phe Asn Asp Trp Asn Pro Glu Ala Asn Pro Leu Glu Arg Tyr
        50                  55                  60 ggc ggc ggc ctg tgg gcc ggt tac gta ccg gga gcg cgc ccg ggc cac     240
Gly Gly Gly Leu Trp Ala Gly Tyr Val Pro Gly Ala Arg Pro Gly His
65                  70                  75                  80 acc tac aag tat cgc atc cgg cac ggc ttc tat cag gcc gac aag acg     288
Thr Tyr Lys Tyr Arg Ile Arg His Gly Phe Tyr Gln Ala Asp Lys Thr
                85                  90                  95 gat ccc tac gcc ttc gcc atg gag ccg cct acc ggc agt ccc atc gaa     336
Asp Pro Tyr Ala Phe Ala Met Glu Pro Pro Thr Gly Ser Pro Ile Glu
                100                 105                 110 ggg ctg gcc tcc atc atc acg cgg ctc gac tac acc tgg cac gac gac     384
Gly Leu Ala Ser Ile Ile Thr Arg Leu Asp Tyr Thr Trp His Asp Asp
            115                 120                 125
```

-continued

| | |
|---|---|
| gaa tgg atg cgg cgc cgg aag ggt ccg gcc agc ctt tac gag ccg gtt<br>Glu Trp Met Arg Arg Arg Lys Gly Pro Ala Ser Leu Tyr Glu Pro Val<br>130               135               140 | 432 |
| tcc atc tac gag gta cat ctg ggc tcc tgg cgt cac aaa cgg ccc ggc<br>Ser Ile Tyr Glu Val His Leu Gly Ser Trp Arg His Lys Arg Pro Gly<br>145               150              155              160 | 480 |
| gag tcc ttc tct tac cgg gag att gcc gag ccg ctg gcc gac tac gtg<br>Glu Ser Phe Ser Tyr Arg Glu Ile Ala Glu Pro Leu Ala Asp Tyr Val<br>               165              170              175 | 528 |
| cag gag atg ggc ttc acg cac gtg gag ctg ctg ccc gtc atg gaa cat<br>Gln Glu Met Gly Phe Thr His Val Glu Leu Leu Pro Val Met Glu His<br>          180               185              190 | 576 |
| ccc tac tac ggc tcc tgg ggc tat cag gtg gtg ggc tac tac gcc cca<br>Pro Tyr Tyr Gly Ser Trp Gly Tyr Gln Val Val Gly Tyr Tyr Ala Pro<br>     195              200              205 | 624 |
| acg ttt cgc tac gga tca ccc cag gac ctg atg tac ctg atc gac tac<br>Thr Phe Arg Tyr Gly Ser Pro Gln Asp Leu Met Tyr Leu Ile Asp Tyr<br>210               215              220 | 672 |
| ctg cac cag cgc ggc atc ggc gtc atc ctc gac tgg gtc ccg agc cac<br>Leu His Gln Arg Gly Ile Gly Val Ile Leu Asp Trp Val Pro Ser His<br>225               230              235              240 | 720 |
| ttt gcg gcc gat ccc cag gga ctg gtt ttc ttc gac ggg acc aca ctc<br>Phe Ala Ala Asp Pro Gln Gly Leu Val Phe Phe Asp Gly Thr Thr Leu<br>               245              250              255 | 768 |
| ttc gaa tac gac gat ccc aag atg cgc tat cac cct gac tgg ggt acg<br>Phe Glu Tyr Asp Asp Pro Lys Met Arg Tyr His Pro Asp Trp Gly Thr<br>          260               265              270 | 816 |
| tat gtg ttc gat tac aac aag ccg ggc gta cgc aac ttt ctg att tcc<br>Tyr Val Phe Asp Tyr Asn Lys Pro Gly Val Arg Asn Phe Leu Ile Ser<br>     275              280              285 | 864 |
| aac gca ctt ttc tgg ctc gaa aag tac cac gtc gac ggg ctg cgc gtc<br>Asn Ala Leu Phe Trp Leu Glu Lys Tyr His Val Asp Gly Leu Arg Val<br>290               295              300 | 912 |
| gat gcg gtg gct tct atg ctc tac cgg gac tac tca cgc aag gag tgg<br>Asp Ala Val Ala Ser Met Leu Tyr Arg Asp Tyr Ser Arg Lys Glu Trp<br>305               310              315              320 | 960 |
| aca ccc aac atc ttc ggc ggc cgt gaa aac ctg gag gcc att gat ttc<br>Thr Pro Asn Ile Phe Gly Gly Arg Glu Asn Leu Glu Ala Ile Asp Phe<br>               325              330              335 | 1008 |
| atc aag aaa ttc aac gaa acg gtc tac ctg cac ttc ccc gag gcc atg<br>Ile Lys Lys Phe Asn Glu Thr Val Tyr Leu His Phe Pro Glu Ala Met<br>          340               345              350 | 1056 |
| acg atc gcc gag gag tcg acg gcc tgg ccc ggc gtg tcg gcc ccc acc<br>Thr Ile Ala Glu Glu Ser Thr Ala Trp Pro Gly Val Ser Ala Pro Thr<br>     355              360              365 | 1104 |
| tac aac aac ggt ctg ggc ttc ctc tac aag tgg aac atg ggc tgg atg<br>Tyr Asn Asn Gly Leu Gly Phe Leu Tyr Lys Trp Asn Met Gly Trp Met<br>370               375              380 | 1152 |
| cac gac acg ctg gac tac atc cag cgc gat ccc atc tac cgc aag tat<br>His Asp Thr Leu Asp Tyr Ile Gln Arg Asp Pro Ile Tyr Arg Lys Tyr<br>385               390              395              400 | 1200 |
| cac cac gac gag ctg acc ttc tcg ctc tgg tac gcc ttt tcg gag cac<br>His His Asp Glu Leu Thr Phe Ser Leu Trp Tyr Ala Phe Ser Glu His<br>               405              410              415 | 1248 |
| tac gtc ctg ccg ctc tcg cac gac gag gtg gtg cac ggc aag ggc tcg<br>Tyr Val Leu Pro Leu Ser His Asp Glu Val Val His Gly Lys Gly Ser<br>          420               425              430 | 1296 |
| ctc tgg ggt aaa atg ccc ggc gac gac tgg cag aag gca gcc aac ttg<br>Leu Trp Gly Lys Met Pro Gly Asp Asp Trp Gln Lys Ala Ala Asn Leu<br>     435              440              445 | 1344 |

```
cgc ctg ctc ttt ggc cac atg tgg ggc cat ccg ggc aaa aaa ctg ctc      1392
Arg Leu Leu Phe Gly His Met Trp Gly His Pro Gly Lys Lys Leu Leu
    450                 455                 460 ttc atg ggc ggc gag ttc ggc cag cac cac gag tgg aac cac gac acg      1440
Phe Met Gly Gly Glu Phe Gly Gln His His Glu Trp Asn His Asp Thr
465                 470                 475                 480 cag ctc gaa tgg cac ctg ctg gac cag ccc tac cat cga ggt att cag      1488
Gln Leu Glu Trp His Leu Leu Asp Gln Pro Tyr His Arg Gly Ile Gln
                485                 490                 495 ctg tgg gtg tgc gat ctg aac cac ctc tac cgt acg aat ccg gcc ctc      1536
Leu Trp Val Cys Asp Leu Asn His Leu Tyr Arg Thr Asn Pro Ala Leu
            500                 505                 510 tgg cac gac gga ccg gaa ggg ttc gag tgg atc gac ttc agc gac cgc      1584
Trp His Asp Gly Pro Glu Gly Phe Glu Trp Ile Asp Phe Ser Asp Arg
        515                 520                 525 gac cag agc gtg atc tgt tac ctg cgc aag aat gcc ggc cgc atg ctg      1632
Asp Gln Ser Val Ile Cys Tyr Leu Arg Lys Asn Ala Gly Arg Met Leu
530                 535                 540 ctg ttc gtg ctg aac ttt acg ccc gtg cca cgc gag cac tac cgc gtg      1680
Leu Phe Val Leu Asn Phe Thr Pro Val Pro Arg Glu His Tyr Arg Val
545                 550                 555                 560 ggc gtg ccg atc ggt ggc ccc tgg cac gag gtg ctc aac agc gac gcg      1728
Gly Val Pro Ile Gly Gly Pro Trp His Glu Val Leu Asn Ser Asp Ala
                565                 570                 575 gtg gcc tac ggc ggg agc ggg atg ggc aac ttc ggc cgc gtc gag gcg      1776
Val Ala Tyr Gly Gly Ser Gly Met Gly Asn Phe Gly Arg Val Glu Ala
            580                 585                 590 gtg ccc gag tcc tgg cac ggc cgc ccc ttc cac tta gag ctg acg ctt      1824
Val Pro Glu Ser Trp His Gly Arg Pro Phe His Leu Glu Leu Thr Leu
        595                 600                 605 ccc ccg ctg gcc gcc ctc atc ctg gag ccg gag cac ggg tag              1866
Pro Pro Leu Ala Ala Leu Ile Leu Glu Pro Glu His Gly
    610                 615                 620

<210> SEQ ID NO 4
<211> LENGTH: 621
<212> TYPE: PRT
<213> ORGANISM: Rhodothermus obamensis

<400> SEQUENCE: 4

Met Ser Trp Leu Thr Glu Glu Asp Ile Arg Arg Trp Glu Ser Gly Thr
1               5                   10                  15

Phe Tyr Asp Ser Tyr Arg Lys Leu Gly Ala His Pro Asp Asp Glu Gly
            20                  25                  30

Thr Trp Phe Cys Val Trp Ala Pro His Ala Asp Gly Val Ser Val Leu
        35                  40                  45

Gly Ala Phe Asn Asp Trp Asn Pro Glu Ala Asn Pro Leu Glu Arg Tyr
    50                  55                  60

Gly Gly Gly Leu Trp Ala Gly Tyr Val Pro Gly Ala Arg Pro Gly His
65                  70                  75                  80

Thr Tyr Lys Tyr Arg Ile Arg His Gly Phe Tyr Gln Ala Asp Lys Thr
                85                  90                  95

Asp Pro Tyr Ala Phe Ala Met Glu Pro Pro Thr Gly Ser Pro Ile Glu
            100                 105                 110

Gly Leu Ala Ser Ile Ile Thr Arg Leu Asp Tyr Thr Trp His Asp Asp
        115                 120                 125

Glu Trp Met Arg Arg Arg Lys Gly Pro Ala Ser Leu Tyr Glu Pro Val
    130                 135                 140
```

Ser Ile Tyr Glu Val His Leu Gly Ser Trp Arg His Lys Arg Pro Gly
145                 150                 155                 160

Glu Ser Phe Ser Tyr Arg Glu Ile Ala Glu Pro Leu Ala Asp Tyr Val
            165                 170                 175

Gln Glu Met Gly Phe Thr His Val Glu Leu Leu Pro Val Met Glu His
        180                 185                 190

Pro Tyr Tyr Gly Ser Trp Gly Tyr Gln Val Val Gly Tyr Tyr Ala Pro
    195                 200                 205

Thr Phe Arg Tyr Gly Ser Pro Gln Asp Leu Met Tyr Leu Ile Asp Tyr
210                 215                 220

Leu His Gln Arg Gly Ile Gly Val Ile Leu Asp Trp Val Pro Ser His
225                 230                 235                 240

Phe Ala Ala Asp Pro Gln Gly Leu Val Phe Phe Asp Gly Thr Thr Leu
                245                 250                 255

Phe Glu Tyr Asp Asp Pro Lys Met Arg Tyr His Pro Asp Trp Gly Thr
            260                 265                 270

Tyr Val Phe Asp Tyr Asn Lys Pro Gly Val Arg Asn Phe Leu Ile Ser
        275                 280                 285

Asn Ala Leu Phe Trp Leu Glu Lys Tyr His Val Asp Gly Leu Arg Val
290                 295                 300

Asp Ala Val Ala Ser Met Leu Tyr Arg Asp Tyr Ser Arg Lys Glu Trp
305                 310                 315                 320

Thr Pro Asn Ile Phe Gly Gly Arg Glu Asn Leu Glu Ala Ile Asp Phe
                325                 330                 335

Ile Lys Lys Phe Asn Glu Thr Val Tyr Leu His Phe Pro Glu Ala Met
            340                 345                 350

Thr Ile Ala Glu Glu Ser Thr Ala Trp Pro Gly Val Ser Ala Pro Thr
        355                 360                 365

Tyr Asn Asn Gly Leu Gly Phe Leu Tyr Lys Trp Asn Met Gly Trp Met
370                 375                 380

His Asp Thr Leu Asp Tyr Ile Gln Arg Asp Pro Ile Tyr Arg Lys Tyr
385                 390                 395                 400

His His Asp Glu Leu Thr Phe Ser Leu Trp Tyr Ala Phe Ser Glu His
                405                 410                 415

Tyr Val Leu Pro Leu Ser His Asp Glu Val Val His Gly Lys Gly Ser
            420                 425                 430

Leu Trp Gly Lys Met Pro Gly Asp Asp Trp Gln Lys Ala Ala Asn Leu
        435                 440                 445

Arg Leu Leu Phe Gly His Met Trp Gly His Pro Gly Lys Lys Leu Leu
450                 455                 460

Phe Met Gly Gly Glu Phe Gly Gln His His Glu Trp Asn His Asp Thr
465                 470                 475                 480

Gln Leu Glu Trp His Leu Leu Asp Gln Pro Tyr His Arg Gly Ile Gln
                485                 490                 495

Leu Trp Val Cys Asp Leu Asn His Leu Tyr Arg Thr Asn Pro Ala Leu
            500                 505                 510

Trp His Asp Gly Pro Glu Gly Phe Glu Trp Ile Asp Phe Ser Asp Arg
        515                 520                 525

Asp Gln Ser Val Ile Cys Tyr Leu Arg Lys Asn Ala Gly Arg Met Leu
530                 535                 540

Leu Phe Val Leu Asn Phe Thr Pro Val Pro Arg Glu His Tyr Arg Val
545                 550                 555                 560

-continued

```
Gly Val Pro Ile Gly Gly Pro Trp His Glu Val Leu Asn Ser Asp Ala
            565             570             575

Val Ala Tyr Gly Gly Ser Gly Met Gly Asn Phe Gly Arg Val Glu Ala
            580             585             590

Val Pro Glu Ser Trp His Gly Arg Pro Phe His Leu Glu Leu Thr Leu
        595             600             605

Pro Pro Leu Ala Ala Leu Ile Leu Glu Pro Glu His Gly
    610             615             620
```